United States Patent [19]

Coates et al.

[11] Patent Number: 5,308,537

[45] Date of Patent: May 3, 1994

[54] MESOGENIC COMPOUNDS

[75] Inventors: David Coates, Dorset; Simon Greenfield, Poole; Ian C. Sage, Dorset, all of Great Britain; Volker Reiffenrath, Rossdorf; Bernhard Rieger, Münster, both of Fed. Rep. of Germany

[73] Assignee: Merck Patent Gesellschaft mit Beschrankter Haftung, Darmstadt, Fed. Rep. of Germany

[21] Appl. No.: 499,539

[22] PCT Filed: Apr. 27, 1990

[86] PCT No.: PCT/EP90/00678

§ 371 Date: Jun. 27, 1990

§ 102(e) Date: Jun. 27, 1990

[87] PCT Pub. No.: WO90/13610

PCT Pub. Date: Nov. 15, 1990

[30] Foreign Application Priority Data

Apr. 28, 1989 [GB] United Kingdom ............... 8909766
Oct. 5, 1989 [GB] United Kingdom ............... 8922486

[51] Int. Cl.⁵ ............ C09K 19/06; C09K 19/12; C09K 19/34; G02F 1/13
[52] U.S. Cl. ............ 252/299.60; 252/299.61; 252/299.62; 252/299.63; 252/299.66; 252/299.67; 252/299.68; 359/103
[58] Field of Search ............ 252/299.61, 299.62, 252/299.63, 299.66, 299.67, 299.68, 299.6; 359/103

[56] References Cited

U.S. PATENT DOCUMENTS

| | | | |
|---|---|---|---|
| 4,330,426 | 5/1982 | Eidenschink et al. | 252/299.63 |
| 4,358,393 | 11/1982 | Zaschke et al. | 252/299.61 |
| 4,382,012 | 5/1983 | Eidenschink et al. | 252/299.1 |
| 4,393,231 | 7/1983 | Misaki et al. | 560/73 |
| 4,871,469 | 10/1989 | Reiffenrath et al. | 252/299.61 |
| 4,880,562 | 11/1989 | Kitano et al. | 252/299.63 |
| 4,886,619 | 12/1989 | Janulis | 252/299.1 |
| 5,082,587 | 1/1992 | Janulis | 252/299.01 |
| 5,190,688 | 3/1993 | Sage et al. | 252/299.01 |

*Primary Examiner*—Richard D. Lovering
*Assistant Examiner*—C. Harris
*Attorney, Agent, or Firm*—Millen, White, Zelano & Branigan

[57] ABSTRACT

Mesogenic compounds with a $\omega$-$CF_3$-alkyl, $\omega$-$CF_3$-alkenyl or $\omega$-$CF_3$-alkinyl terminal group of formula I

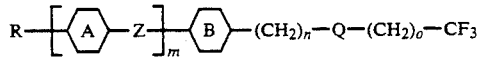

with the meaning of R, Z, Q,

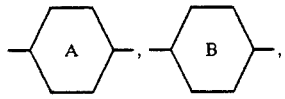

m, n and o being indicated in claim 1.

2 Claims, No Drawings

MESOGENIC COMPOUNDS

The invention relates to mesogenic compounds with a ω-CF₃-alkyl, ω-CF₃-alkenyl or ω-CF₃-alkinyl terminal group of formula I

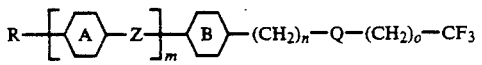

wherein R is unsubstituted, a mono cyano or trifluoromethyl substituted or a mono-, oligo- or polyhalogeno-substituted alkyl or alkenyl residue having 1 to 15 carbon atoms, or such a residue wherein one or more $CH_2$ groups are each independently replaced by —O—, —CO—, —CO—O—, —O—CO— or —O—CO—O— with the proviso that oxygen atoms are not directly attached to each other, the rings A and B independently are
 (a) a tarns-1,4-cyclohexylene group, wherein one or two non-adjacent $CH_2$ groups may also be replaced by —O— and/or —S— or one or two CH groups may be also be replaced by N,
 (b) a 1,4-phenylene group, wherein one or two CH groups may also be replaced by N,
 (c) a group selected from 1,4-bicyclo(2,2,2)octylene, 1,4-cyclohexenylene, naphthalin-2,6-diyl and 1,3-cyclobutylene, it being possible for groups (a) and (b) to be substituted by one or more of halogen, cyano or methyl, Z is independently from each other —CO—O—, —O—CO—, —CH₂CH₂—, —CH₂O—, —OCH₂—, —C≡C—, —N=CH— or a single bond, Q is a single bond, —CH=CH— or —C≡C—, m is 1, 2 or 3, and n and o are independently from each other zero or intergers of 1 to 10, with the proviso that in case Q is a single bond n+o≧1.

The invention further relates to liquid crystalline media comprising at least two liquid crystalline components at least one of which being a compound of formula I, further to electro-optical system containing such media and to the use of the compounds of formula I as components of liquid crystalline media.

For simplicity, in the following text Phe is a 1,4-phenylene group, Cyc a trans-1,4-cyclohexylene group, Che a 1,4-cyclohexenylene group, Dio a dioxane-2,5-diyl group, Dit a dithane-2.5-diyl group. Pyr a pyrimidine-1,5-diyl group, Pyd a pyridine-2,5-diyl group, Pyz a pyrazine-2,5-diyl group, Pyn a pyridazine-3,6-diyl group, Pip a piperidine-1,4-diyl group and Thp a tetrahydropyrane-2,5-diyl group. These groups may be substituted by one or more of halogen, cyano or methyl. The substituted groups are denoted by adding the chemical symbol of the substituent to the respective abbreviation of the unsubstituted group. PheF, for example, means a 1,4-phenylene group monosubstituted by a F atom

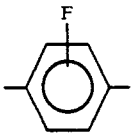

and Phe3F5F is a 3,5-difluoro-1,4-phenylene group.

The denotations for the unsubstituted and substituted groups include all constitutional isomers.

The compounds of the formula I can be used as components of liquid crystal media, in particular for electro-optical systems and liquid crystal displays, based on the principle of the twisted nematic cell including cells with twist angles different from 90° (e.g. STN, SBE, or OMI), the guest-host effect, the effect of deformation of aligned phases or the effect of dynamic scattering. Due to their superior stability versus heat and light the compounds of formula I are especially suited for active matrix addressed displays.

The invention was based on the object of discovering new liquid crystal or mesogenic compounds being suited as components of liquid crystal media and especially exhibiting a broad mesophase range, a rather low viscosity, a high stability versus chemicals and thermal and electromagnetical energy, especially versus UV-light and light of the short wavelength range of the visible spectrum, advantageous values for the elastic constants, the optical and dielectric anisotropy, a good electrooptical and thermooptical response and a good miscibility with other, including known liquid crystal compounds.

It has been found, that the compounds of formula I are outstandingly suitable as components of liquid crystalline media. In particular, liquid crystalline media having a broad mesophase range, a rather low viscosity and a high stability versus chemicals, heat and light and advantageous values of the optical and dielectric anisotropy can be prepared with the aid of these compounds.

By providing the compounds of the formula I, the range of liquid crystal substances which are suitable under various technological aspects for the preparation of liquid crystal media is moreover quite generally considerable extended.

The compounds of the formula I have a wide range of application. Depending on the choice of the substituents, there compounds can be used as base materials of which liquid crystal media are predominantly composed; however, compounds of the formula I can also be added to liquid crystal base materials of other classes of compounds, for example in order to vary the elastic constants, the dielectric and/or optical anisotropy and/or the viscosity and/or the phase range of such dielectric.

The compounds of the formula I are furthermore suitable as intermediates for the preparation of other substances which can be used as constituents of liquid crystal dielectrics.

The compounds of the formula I are colourless in the pure state and form liquid crystal mesophases in a temperature range which is favourably located for electrooptical use. They are very stable towards chemicals, heat and light and exhibit advantageous values for the optical and dielectric anisotropy, the elastic constants, the phase range and the viscosity and they exhibit a good electrooptical and thermooptical response and a good miscibility with other liquid crystal compounds.

The invention thus relates to compounds of the formula I and to the use of the compounds of the formula I as components of liquid crystalline media. The invention furthermore relates to liquid crystalline media containing at least one compound of the formula I and to liquid crystal displays containing such media.

Above and below R, the rings A and B, Z, Q, m, n and o have the meaning given, unless expressly indicated otherwise.

The compounds of the formula I accordingly include compounds with a ω-CF$_3$-alkyl, a ω-CF$_3$-alkenyl and a ω-CF$_3$-alkinyl group according to formulae Ia, Ie and Ii

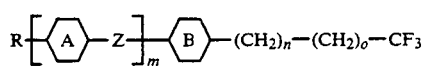

Ia

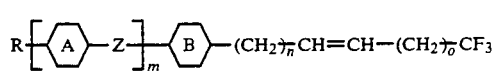

Ie

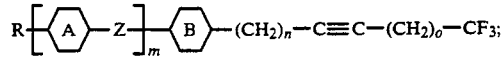

Ii these formulae comprise binuclear, trinuclear and tetranuclear compounds of the formulae Ia2-Ia4, Ie2-Ie4 and Ii2-Ii4.

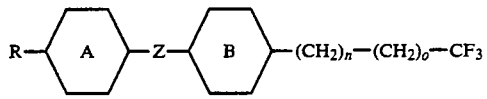

Ia2

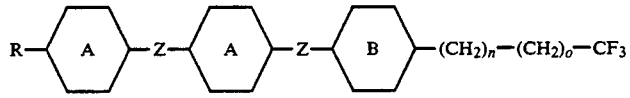

Ia3

Ia4

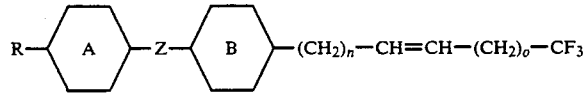

Ie2

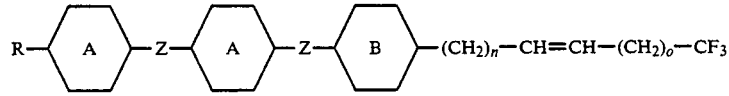

Ie3

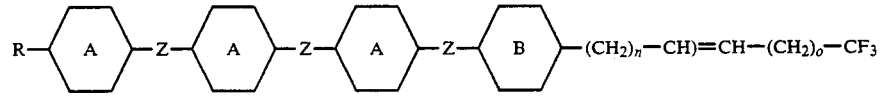

Ie4

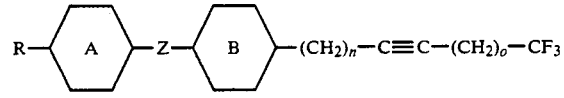

Ii2

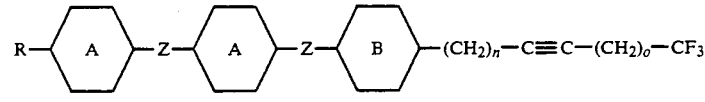

Ii3

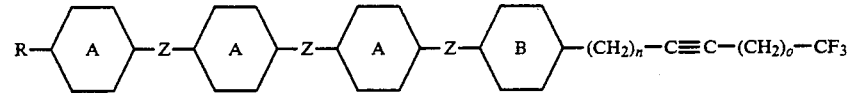

Ii4

In the compounds of the formulae Ia the CF$_3$-group is not directly linked to ring B (n+o≧1) and the chain length is preferably given via 1≦n+o≦13 and in particular via 1≦n+o≦10. In the compounds of formulae Ie and Ii n and o are independently from each other 0–10 and, in particular, 0–7 and the chain length of the ω-CF$_3$-alkenyl resp. ω-CF$_3$-alkinyl group is preferably given via 0≦n+o≦12.

In the compounds of the formula Ia, Ie and Ii the ring A preferably denotes Cyc, Phe, PheF, PheF$_2$, Dio, Che, Pym or Pyr and especially Cyc, Phe, Phe2F, Phe3F, Phe2F3F and Dio and Che; the ring B preferably is Cyc, Phe, PheF, PheF$_2$, Dio and Che with PheF resp. PheF$_2$ preferably denoting Phe2F, Phe3F resp. Phe2F3F and Phe3F5F.

The compounds of formulae Ia, Ie and Ii preferably contain not more than one of the radicals Dio, Dit, Pip, Bi, Pyn or Pyr.

In the compounds of formula Ia, Ie and Ii Z preferably denotes independently from each other a single bond, —COO—, —OOC—, —C≡C— or —CH₂CH₂—, especially a single bond, —COO—, —OOC— or —CH₂CH₂— and, in particular, a single bond or —CH₂CH₂—. In case m+3 at least one Z preferably denotes a single bond.

The compounds of formula Ia, Ie and Ii preferably contain 2 or 3 rings. 4-ring compounds, however, are especially suited as high clearing point additives for liquid crystalline media. In order to increase their miscibility with other liquid crystalline compounds and/or to decrease their flow viscosity compounds with 4 rings preferably contain at least one laterally substituted ring A or B and especially at least one group chosen from Phe2F, Phe3F, Phe2F₃F and Phe3F5F.

In the compounds of the formula Ia, Ie and Ii, those stereoisomers in which the rings Cyc and Pip are trans-1,4-disubstituted and/or Dio and Dit are trans-2,5-disubstituted are preferred. Those of the formulae mentioned above and below which contain one or more groups Dio, Dit, Pip, Pyd and/or Pyr include in each case the two 2,5-(Dio, Dit, Pyd or Pyr) or 1,4-position isomers (Pip). Che comprises in each case 1,4-cyclohex-1-enylene and 1,4-cyclohex-3-enylene.

In the compounds of the formulae Ia, Ie and Ii in which one of the rings represents a Pyd, Pyr or Pyz ring, R is preferably alkyl or alkoxy.

Compounds of the formula Ia, Ie and Ii the ω-CF₃ terminal group of which exhibits an odd number of C atoms, that is an even number for n+o, are preferred; n+o in particular is 0, 2, 4 or 6. Secondly preferable n+o is odd and exhibits the values 1, 3, 5 and 7. The elastic constants of the compounds of the formula Ia, Ie and Ii can be influenced and optimized by varying the length of the side chain with the terminal CF₃ group; thus it is possible, for example, to provide compounds, resp. liquid crystalline media containing these compounds exhibiting improved values of the threshold voltage and/or the steepness of the electrooptical characteristic line.

The terminal substituent R in the compounds of formulae Ia2–Ia4, Ie2–Ie4 and Ii2–Ii4 preferably contains 1–13 C atoms and in particular 1–11 C atoms. It is also possible for one or more CH groups in R to be replaced. Preferably, only one CH₂ group is replaced by —O—, —CO—, —OCO—, —COO— or —OCOO—, in particular by —O—, —CO—, —OCO— or —COO—.

If R is an alkyl radical in which one ("alkoxy" or "oxaalkyl") or two ("alkoxyalkoxy" or dioxaalkyl") non-adjacent CH₂ groups can also be replaced by O atoms, it can be straight-chain or branched. Preferably, it is straight-chain, has 2, 3, 4, 5, 6 or 7 C atoms and is preferably ethyl, propyl, butyl, pentyl, hexyl, heptyl, ethoxy, propoxy, butoxy, pentoxy, hexoxy, or heptoxy, or furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy, tetradecoxy or pentadecoxy.

Oxaalkyl is preferably straight-chain 2-oxapropyl (=methoxymethyl), 2- (=ethoxymethyl) or 3-oxabutyl (=2-methoxymethyl, 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4-, 2,4-dioxapentyl, 1,3-, 1,4-, 1,5-, 2,4-, 2,5- or 3,5-dioxahexyl, 1,3-, 1,4-, 1,5-, 1,6-, 2,4-, 2,5-, 2,6-, 3,5-, 3,6- or 4,6-dioxaheptyl. If R is an alkyl radical in which a CH₂ group is replaced by —O—CO— or —CO—O—, this can be straight-chain or branched. Preferably, it is straight-chain and has 2 to 6C atoms. It is accordingly in particular acetyloxy, propionyloxy, butyryloxy, pentanoyloxy, hexanoyloxy, acetyloxymethyl, propionyloxymethyl, butyryloxymethyl, pentanoyloxymethyl, 2-acetyloxymethyl, 2-propionyloxyethyl, 2-butyryloxyethyl, 3-acetyloxymethyl, 3-propionyloxyethyl, 2-butyryloxyethyl, 3-acetyloxymethyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(proppoxycarbonyl)ethyl, 3-(methoxycarbonyl)propyl, 3-(ethoxycarbonyl)propyl or 4-(methoxycarbonyl)butyl.

If R is a mono-, oligo- or polyhalogeno substituted alkyl radical, this can be straight-chain or branched. Preferably it is straight-chain, has 3–12 C atoms and is mono-, di-, tri- or tetrahalogenated, particular preferably with F and/or Cl. R preferably is 2-fluoroethyl, 2,2-difluoroethyl, 2,2,2-trifluoroethyl, 2-fluoropropyl, 3,3,3-trifluoropropyl, 2,3-difluoropropyl, 2-chlorobutyl, 4,4,4-trifluorobutyl, 4,5-difluoropentyl, 5-fluoropentyl, 5,5-difluoropentyl, 5,5,5-trifluoropentyl, 5,5,5-trifluoro-3-fluoro-pentyl, 6,6,6-trifluorohexyl, 6-fluorohexyl, 6-chlorohexyl, 6,6-difluorohexyl, 6-fluorohexyl, 6-chlorohexyl, 6,6-fifluorohexyl, 7,7,7-trifluoroheptyl, 3,5-difluoroheptyl, 7-chloroheptyl, 7,7-dichloroheptyl, 8,8-difluoroocyl, 8,8,8-trifluoroocyl, 8-chloroocyl and 9,9,9-trifluorononyl.

"Symmetrical" compounds exhibiting identical terminal groups are furthermore preferred.

Formulae Ia, Ie and Ii include both the racemates of these compounds and the optical antipodes as well as mixtures thereof.

Amongst the compounds of the formulae Ia, Ie and Ii, those in which at least one of the radicals contained therein has one of the preferred meanings given are preferred.

Compounds of the formula I exhibiting for the unit

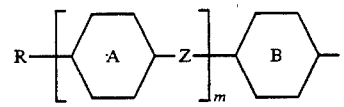

one of the following structures are preferred:

| a) Binuclear structures | |
|---|---|
| R—Cyc—Phe(F)— | I2-1 |
| R—Phe—PheF₂— | I2-2 |
| R—Phe2F—Phe— | I2-3 |
| R—Phe—Cyc— | I2-4 |
| R—Phe3F—Phe— | I2-5 |
| R—Phe—Phe2F— | I2-6 |
| R—Phe—Phe3F— | I2-7 |
| R—PheF₂—Phe— | I2-8 |
| R—Cyc—Cyc— | I2-9 |
| R—Cyc—Dio— | I2-10 |
| R—Phe—Dio— | I2-11 |
| R—Dio—Phe(F)— | I2-12 |
| R—Che—Phe(F)— | I2-13 |
| R—Phe—Che— | I2-14 |
| R—Cyc—Che— | I2-15 |

-continued

| | |
|---|---|
| R—Che—Cyc— | I2-16 |
| R—Cyc—COO—Phe(F)— | I2-17 |
| R—Cyc—CH₂CH₂—Phe(F)— | I2-18 |
| R—Phe—C≡C—Phe(F)— | I2-19 |
| R—Cyc—OOC—Phe(F)— | I2-20 |
| R—Pyr—CH₂CH₂—Phe(F)— | I2-21 |
| R—Phe(F)—COO—Phe(F)— | I2-22 |
| R—PheF₂—COO—Phe— | I2-23 |
| R—Pyn—Phe(F)— | I2-24 |
| R—Pyr—Phe(F)— | I2-25 |
| R—Phe(F)—OOC—Phe(F)— | I2-26 |
| R—Phe—Phe— | I2-27 |
| R—Dio—Cyc— | I2-28 |
| b) Trinuclear structures | |
| R—Cyc—Cyc—Phe— | I3-1 |
| R—Cyc—Cyc—PheF— | I3-2 |
| R—Cyc—Cyc—PheF₂— | I3-3 |
| R—Cyc—Cyc—Dio— | I3-4 |
| R—Cyc—Phe—Phe— | I3-5 |
| R—Cyc—PheF—Phe— | I3-6 |
| R—Cyc—Phe—PheF— | I3-7 |
| R—Cyc—Phe—PheF₂— | I3-8 |
| R—Cyc—PheF—PheF— | I3-9 |
| R—Cyc—Cyc—Che— | I3-10 |
| R—Cyc—Che—Phe(F)— | I3-11 |
| R—Dio—Phe—Phe(F)— | I3-12 |
| R—Phe—Phe—Phe— | I3-13 |
| R—Phe—PheF—Phe— | I3-14 |
| R—Phe—Phe—PheF— | I3-15 |
| R—Phe—COO—Phe(F)—Phe(F)— | I3-16 |
| R—Phe—OOC—Phe(F)—Phe(F)— | I3-17 |
| R—Cyc—CH₂CH₂—Cyc—Cyc— | I3-18 |
| R—Cyc—Cyc—OOC—Cyc— | I3-19 |
| R—Cyc—Cyc—COO—Cyc— | I3-20 |
| R—Cyc—Pyr—Phe(F)— | I3-21 |
| R—Cyc—CH₂CH₂—Phe(F)—Phe(F)— | I3-22 |
| R—Dio—Phe—COO—Phe(F)— | I3-23 |
| R—Cyc—COO—Phe—Phe(F)— | I3-24 |
| R—Pyr—PheF—Cyc— | I3-25 |
| R—Pyr—Phe—OCH₂—Cyc— | I3-26 |
| R—Phe—COO—Phe(F)—COO—Phe(F)— | I3-27 |
| R—Phe—CH₂CH₂—Phe(F)—Phe(F)— | I3-28 |
| R—Cyc—Phe—C≡C—Phe(F)— | I3-29 |
| R—Cyc—Cyc—CH₂CH₂—Phe— | I3-30 |
| R—Cyc—Cyc—CH₂CH₂—PheF— | I3-31 |
| R—Cyc—CH₂CH₂—Cyc—Phe(F)— | I3-32 |
| R—Phe—Phe(F)—CH₂CH₂—Phe(F)— | I3-33 |
| R—Phe—CH₂CH₂—Phe(F)—PheF— | I3-34 |
| R—Cyc—Phe—Cyc— | I3-35 |
| R—Phe—Cyc—Cyc— | I3-36 |
| R—Phe—Phe—Cyc— | I3-37 |
| R—Phe—Phe—Dio— | I3-38 |
| c) Tetranuclear structures | |
| R—Cyc—Phe—Phe—Cyc— | I4-1 |
| R—Cyc—PheF—Phe—Cyc— | I4-2 |
| R—Cyc—Phe—PheF—Cyc— | I4-3 |
| R—Cyc—Cyc—Cyc—Phe— | I4-4 |
| R—Cyc—Cyc—Cyc—PheF— | I4-5 |
| R—Cyc—Cyc—Che—Phe(F)— | I4-6 |
| R—cyc—Cyc—Phe(F)—Dio— | I4-7 |
| R—Cyc—Cyc—Dio—Phe(F)— | I4-8 |
| R—Cyc—Cyc—COO—Phe(F)—Phe(F)— | I4-9 |
| R—Cyc—Cyc—CH₂CH₂—Phe(F)—Phe(F)— | I4-10 |
| R—Cyc—Cyc—CH₂CH₂—Cyc—Cyc— | I4-11 |
| R—Phe—Phe(F)—Phe— | I4-12 |

Compounds of the formula I exhibiting one of the preferred structures I2-1 - I2-27, I3-1 - I3-34 and I4-1 - I4-12 are preferred. These compounds comprise binuclear, trinuclear and tetranuclear compounds with one of the terminal groups being in each case a ω-CF₃-alkyl group, a ω-CF₃-alkenyl group or a ω-CF₃-alkinyl group.

The compounds according to formula I with a ω-CF₃-alkyl, ω-CF₃-alkenyl or ω-CF₃-alkinyl group and especially with a ω-CF₃-alkyl or a ω-CF₃-alkenyl group are chemically very stable and they exhibit a high temperature and UV stability superior to that of cyano compounds for example.

The compounds of formula I with a ω-CF₃-alkyl, ω-CF₃-alkenyl or ω-CF₃-alkinyl group are further characterized by a relatively high or even high dielectric anisotropy. These compounds are therefore very well suited as components of liquid crystalline media which are used in displays based on the principle of the twisted nematic cell. The term twisted nematic cell is used here in a wide sense and comprises cells with twist angles ranging from 0° to 360° such as, for example, TN (twisted nematic), supertwisted nematic (STN), supertwisted birefringence (SBE) or low twisted nematic (LTN, β<90°) cells. Due to their high stability the ω-CF₃-alkyl, ω-CF₃-alkenyl and ω-CF₃-alkinyl compounds are especially preferred for active matrix addressed displays. It is also possible, however, for these compounds to be used in displays based on the guest-host effect, the effect of deformation of aligned phases or the effect of dynamic scattering.

ω-CF₃-alkyl, ω-CF₃-alkenyl and ω-CF₃-alkinyl compounds exhibiting the binuclear or trinuclear structures of formulae I2-1 - I2-27 and I3-1 - I3-34 are preferred; the tetranuclear compounds with the structures I4-1 - I4-11 are secondly preferred.

The properties of the ω-CF₃-alkyl, ω-CF₃-alkenyl and ω-CF₃-alkinyl compounds according to formula I can be varied to a great extent and readily be optimized with respect to the intended application by properly chosing the rings A and B. ω-CF₃-alkyl, ω-CF₃-alkenyl and ω-CF₃-alkinyl compounds and especially ω-CF₃-alkyl compounds with the structures I2-9, I2-10, I2-15, I2-16, I3-1 - I3-4, I3-10, I3-11, I3-18 - I3-20, I3-30 -I3-32, I4-4 - I4-8 and I4-11, for example, are characterized by rather low or even low values of the optical anisotropy.

These compounds are well suited, for example, for liquid crystalline media for TN displays being operated under the so-called first-minimum condition and especially for low-Δn-TFT applications.

Contrary to these compounds with a ω-CF₃-alkyl, ω-CF₃-alkenyl and a ω-CF₃-alkinyl group being composed of aromatic rings mainly or exclusively such as, for example, compounds exhibiting the structures I2-2, I2-3, I2-5 - I2-8, I2-19, I2-21 - I2-26, I3-13 - I3-17, I3-27, I3-28, I3-33, I3-34 and I4-12 are generally characterized by rather high or even high values of Δn. Especially preferred for high-Δn applications are compounds with a ω-CF₃-alkenyl or a ω-CF₃-alkinyl terminal group and one of the preferred high-Δn structures enumerated above.

ω-CF₃-alkyl compound exhibiting a 3-fluoro- or a 3,5-difluoro-1,4-phenylene group for the rings A and/or B are usually characterized by high or even very high values of the dielectric anisotropy and can be used to increase the dielectric anisotropy and hence to lower the threshold voltage of liquid crystalline media.

The threshold voltage is further influenced by the elastic constants of the liquid crystalline compounds. The threshold voltage of a TN structure, for example, is given via $$V_{th} = \pi \left( \frac{k'}{\epsilon_0 \Delta\epsilon} \right)^{\frac{1}{2}}$$

wherein $\epsilon_0$ is the dielectric constant of the vacuum, $\Delta\epsilon$ is the dielectric anisotropy of the liquid crystal and k' denotes an elastic constant primarily dependent on the splay elastic constant $k_{11}$. Since the dioxane-2,5-diyl group, for example, exhibits rather low values for $k_{11}$ the compounds of formulae I2-10, I2-11, I3-4, I4-7 and I4-8 are advantageously used for low threshold voltage TN displays. The elastic constants of the $\omega$-CF$_3$-alkyl compounds can further be modified to a great extent by varying the chain length of the $\omega$-CF$_3$-alkyl group $$-(CH_2)_n-(CH_2)_o-CF_3$$

or the position of the double bond resp. the triple bond in the $\omega$-CF$_3$-alkenyl resp. $\omega$-CF$_3$-alkinyl terminal group and/or the chain length of these terminal groups:

$$-(CH_2)_n-CH=CH-(CH_2)_o-CF_3$$

$$-(CH_2)_n-C\equiv C-(CH_2-CF_3$$

Thus it is possible to optimize the elastic properties of the $\omega$-CF$_3$-alkyl, the $\omega$-CF$_3$-alkenyl and $\omega$-CF$_3$-alkinyl compounds not only for TN applications which were merely considered as an example but also for other applications.

Compounds of the formula I wherein one terminal group is a $\omega$-CF$_3$-alkyl, $\omega$-CF$_3$-alkenyl or a $\omega$-CF$_3$-alkinyl group and the other terminal group is a straight-chain or not more than a singly branched alkyl or alkoxy group with 1-12, in particular 2-10 C atoms are especially preferred. In the compounds of formula I n preferably denotes 0-8, particular 0-6 and is preferably even. Compounds exhibiting an odd number for n are secondly preferred.

The following smaller group of compounds of formula I with a $\omega$-CF$_3$-alkyl terminal group in which Phe-F is 1,4-phenylene which is substituted in 2- or 3-position, PheF$_2$ is 1,4-phenylene which is substituted in 2- and 3- or 3- and 5-position and in which the other abbreviations have the meaning indicated above are particularly preferred. In these compounds alkyl is preferably unsubstituted straight-chain methyl, ethyl, propyl, butyl, pentyl and hexyl. Alkoxy is preferably unsubstituted straight-chain methoxy, ethoxy, propoxy, butoxy, pentoxy and hexoxy. Alkanoyloxy is preferably unsubstituted straight-chain acetoxy, propanoyloxy, butanoyloxy, pentanoyloxy and hexanoyloxy. If the alkyl, alkoxy or alkanoyloxy groups are substituted they are preferably fluorinated. Especially preferred are those groups exhibiting a terminal trifluorinated C atom. n is preferably 1, 2, 3, 4 and 5, particularly preferably 1, 2 and 3 and especially 2.

I alkyl-Phe-Phe-(CH$_2$)$_n$—(CH$_2$)$_o$—CF$_3$
alkyl-Phe-PheF-(CH$_2$)$_n$—(CH$_2$)$_o$—CF$_3$
alkyl-PheF-Phe-(CH$_2$)$_n$—(CH$_2$)$_o$—CF$_3$
alkyl-Phe-PheF$_2$-(CH$_2$)$_n$—(CH$_2$)$_o$—CF$_3$
alkoxy-Phe-Phe-(CH$_2$)$_n$—(CH$_2$)$_o$—CF$_3$
alkoxy-Phe-PheF-(CH$_2$)$_n$—(CH$_2$)$_o$—CF$_3$

II alkyl-Cyc-Phe-(CH$_2$)$_n$—(CH$_2$)$_o$—CF$_3$
alkyl-Cyc-PheF-(CH$_2$)$_n$—(CH$_2$)$_o$—CF$_3$
alkoxy-Cyc-Phe-(CH$_2$)$_n$—(CH$_2$)$_o$—CF$_3$
alkanoyloxy-Cyc-Phe-(CH$_2$)$_n$—(CH$_2$)$_o$—CF$_3$
alkyl-Phe-Cyc-(CH$_2$)$_n$—(CH$_2$)$_o$—CF$_3$
alkyl-PheF-Cyc-(CH$_2$)$_n$—(CH$_2$)$_o$—CF$_3$
alkoxy-Phe-Cyc-Phe-Cyc-(CH$_2$)$_n$—(CH$_2$)$_o$—CF$_3$
alkanoyl-Phe-Cyc-Phe-Cyc-(CH$_2$)$_n$—(CH$_2$)$_o$—CF$_3$

III alkyl-Phe-COO-Phe-(CH$_2$)$_n$—(CH$_2$)$_o$—CF$_3$
alkyl-Phe-COO-PheF-(CH$_2$)$_n$—(CH$_2$)$_o$—CF$_3$
alkyl-Phe-COO-PheF$_2$-(CH$_2$)$_n$—(CH$_2$)$_o$—CF$_3$
alkoxy-Phe-COO-PheF-(CH$_2$)$_n$—(CH$_2$)$_o$—CF$_3$

IV alkyl-Cyc-CH$_2$CH$_2$-Phe-(CH$_2$)$_n$—(CH$_2$)$_o$—CF$_3$
alkoxy-Cyc-CH$_2$CH$_2$-Phe-(CH$_2$)$_n$—(CH$_2$)$_o$—CF$_3$
alkyl-Cyc-CH$_2$CH$_2$-PheF-(CH$_2$)$_n$—(CH$_2$)$_o$—CF$_3$
alkoxy-Cyc-CH$_2$CH$_2$-PheF-(CH$_2$)$_n$—(CH$_2$)$_o$—CF$_3$
alkyl-Cyc-CH$_2$CH$_2$-Che-(CH$_2$)$_n$—(CH$_2$)$_o$—CF$_3$
alkyl-Cyc-CH$_2$CH$_2$-Dio-(CH$_2$)$_n$—(CH$_2$)$_o$—CF$_3$

V alkyl-Cyc-Cyc-(CH$_2$)$_n$—(CH$_2$)$_o$—CF$_3$
alkoxy-Cyc-Cyc-(CH$_2$)$_n$—(CH$_2$)$_o$—CF$_3$
alkanoyloxy-Cyc-Cyc-(CH$_2$)$_n$—(CH$_2$)$_o$—CF$_3$

VI alkyl-Cyc-Che-(CH$_2$)$_n$—(CH$_2$)$_o$—CF$_3$
alkoxy-Cyc-Che-(CH$_2$)$_n$—(CH$_2$)$_o$—CF$_3$
alkanoyloxy-Cyc-Che-(CH$_2$)$_n$—(CH$_2$)$_o$—CF$_3$
alkyl-Cyc-Dio-(CH$_2$)$_n$—(CH$_2$)$_o$—CF$_3$
alkoxy-Cyc-Dio-(CH$_2$)$_n$—(CH$_2$)$_o$—CF$_3$
alkanoyloxy-Cyc-Dio-(CH$_2$)$_n$—(CH$_2$)$_o$—CF$_3$

VII alkyl-Cyc-COO-Phe-(CH$_2$)$_n$—(CH$_2$)$_o$—CF$_3$
alkyl-Cyc-COO-PheF-(CH$_2$)$_n$—(CH$_2$)$_o$—CF$_3$
alkyl-Cyc-COO-PheF$_2$-(CH$_2$)$_n$—(CH$_2$)$_o$—CF$_3$
alkoxy-Cyc-COO-Phe-(CH$_2$)$_n$—(CH$_2$)$_o$—CF$_3$
alkoxy-Cyc-COO-PheF-(CH$_2$)$_n$—(CH$_2$)$_o$—CF$_3$
alkanoyloxy-Cyc-COO-Phe-(CH$_2$)$_n$—(CH$_2$)$_o$—CF$_3$
alkanoyloxy-Cyc-COO-PheF-(CH$_2$)$_n$—(CH$_2$)$_o$—CF$_3$

VIII alkyl-Cyc-CH$_2$CH$_2$-Phe-Phe-(CH$_2$)$_n$—(CH$_2$)$_o$—CF$_3$
alkyl-Cyc-CH$_2$CH$_2$-Phe-PheF-(CH$_2$)$_n$—(CH$_2$)$_o$—CF$_3$
alkoxy-Cyc-CH$_2$CH$_2$-Phe-Phe-(CH$_2$)$_n$—(CH$_2$)$_o$—CF$_3$
alkoxy-Cyc-CH$_2$CH$_2$-Phe-PheF-(CH$_2$)$_n$—(CH$_2$)$_o$—CF$_3$

IX alkyl-Cyc-Cyc-Phe-(CH$_2$)$_n$—(CH$_2$)$_o$—CF$_3$
alkoxy-Cyc-Cyc-Phe-(CH$_2$)$_n$—(CH$_2$)$_o$—CF$_3$
alkanoyloxy-Cyc-Cyc-Phe-(CH$_2$)$_n$—(CH$_2$)$_o$—CF$_3$
alkyl-Cyc-Cyc-PheF-(CH$_2$)$_n$—(CH$_2$)$_o$—CF$_3$
alkoxy-Cyc-Cyc-PheF-(CH$_2$)$_n$—(CH$_2$)$_o$—CF$_3$
alkyl-Cyc-Cyc-PheF$_2$-(CH$_2$)$_n$—(CH$_2$)$_o$—CF$_3$
alkoxy-Cyc-Cyc-PheF$_2$-(CH$_2$)$_n$—(CH$_2$)$_o$—CF$_3$
alkyl-Cyc-Cyc-Che-(CH$_2$)$_n$—(CH$_2$)$_o$—CF$_3$
alkyl-Cyc-Cyc-Dio-(CH$_2$)$_n$—(CH$_2$)$_o$—CF$_3$
alkyl-Cyc-Cyc-Cyc-(CH$_2$)$_n$—(CH$_2$)$_o$—CF$_3$
alkoxy-Cyc-Cyc-Cyc-(CH$_2$)$_n$—(CH$_2$)$_o$—CF$_3$
alkyl-Cyc-Phe-Cyc-(CH$_2$)$_n$—(CH$_2$)$_o$—CF$_3$
alkoxy-Cyc-Phe-Cyc-(CH$_2$)$_n$—(CH$_2$)$_o$—CF$_3$
alkanoyloxy-Cyc-Phe-Cyc-(CH$_2$)$_n$—(CH$_2$)$_o$—CF$_3$ alkyl-Phe-Phe-Cyc-(CH₂)ₙ—(CH₂)ₙ—(CH₂)ₒ—CF₃
alkoxy-Phe-Phe-Cyc-(CH₂)ₙ—(CH₂)ₙ—(CH₂)ₒ—CF₃
alkanoyloxy-Phe-Phe-Cyc-(CH₂)ₙ—(CH₂)ₙ—(CH₂)ₒ—CF₃
alkyl-Phe-Cyc-Cyc-(CH₂)ₙ—(CH₂)ₒ—CF₃
alkoxy-Phe-Cyc-Cyc-(CH₂)ₙ—(CH₂)ₒ—CF₃
alkanoyloxy-Phe-Cyc-Cyc-(CH₂)ₙ—(CH₂)ₒ—CF₃
alkyl-Cyc-Phe-Dio-(CH₂)ₙ—(CH₂)ₒ—CF₃
alkoxy-Cyc-Phe-Dio-(CH₂)ₙ—(CH₂)ₒ—CF₃
alkanoyloxy-Cyc-Phe-Dio-(CH₂)ₙ—(CH₂)ₒ—CF₃

X alkyl-Cyc-Phe-Phe-(CH₂)ₙ—(CH₂)ₒ—CF₃
alkyl-Cyc-Phe-PheF-(CH₂)ₙ—(CH₂)ₒ—CF₃
alkyl-Cyc-PheF-Phe-(CH₂)ₙ—(CH₂)ₒ—CF₃
alkoxy-Cyc-Phe-Phe-(CH₂)ₙ—(CH₂)ₒ—CF₃
alkanoyloxy-Cyc-Phe-Phe-(CH₂)ₙ—(CH₂)ₒ—CF₃

XI alkyl-Phe-Phe-OOC-Phe-(CH₂)ₙ—(CH₂)ₒ—CF₃
alkyl-Phe-Phe-OOC-PheF-(CH₂)ₙ—(CH₂)ₒ—CF₃
alkyl-Phe-PheF-OOC-Phe-(CH₂)ₙ—(CH₂)ₒ—CF₃
alkoxy-Phe-Phe-OOC-Phe-(CH₂)ₙ—(CH₂)ₒ—CF₃
alkoxy-Phe-Phe-OOC-PheF-(CH₂)ₙ—(CH₂)ₒ—CF₃

XII alkyl-Cyc-Cyc-COO-Phe-(CH₂)n—(CH2)ₒ—CF₃
alkyl-Cyc-Cyc-COO-PheF-(CH₂)n—(CH2)ₒ—CF₃
alkoxy-Cyc-Cyc-COO-Phe-(CH₂)n—(CH2)ₒ—CF₃
alkoxy-Cyc-Cyc-COO-PheF-(CH₂)n—(CH2)ₒ—CF₃
alkanoyloxy-Cyc-Cyc-COO-Phe-(CH₂)n—(CH2)ₒ—CF₃

XIII alkyl-Cyc-Phe-COO-Phe-(CH₂)n—(CH2)ₒ—CF₃
alkyl-Cyc-Phe-COO-PheF-(CH₂)n—(CH2)ₒ—CF₃
alkyl-Cyc-Phe-COO-PheF₂-(CH₂)n—(CH2)ₒ—CF₃
alkoxy-Cyc-Phe-COO-Phe-(CH₂)n—(CH2)ₒ—CF₃
alkoxy-Cyc-Phe-COO-PheF-(CH₂)n—(CH2)ₒ—CF₃
alkanoyloxy-Cyc-Phe-COO-Phe-(CH₂)n—(CH2)ₒ—CF₃
alkanoyloxy-Cyc-Phe-COO-PheF-(CH₂)n—(CH2)ₒ—CF₃

XIV alkyl-Phe-COO-Phe-COO-Phe-(CH₂)n—(CH2)ₒ—CF₃
alkyl-Phe-COO-Phe-COO-PheF-(CH₂)n—(CH2)ₒ—CF₃
alkoxy-Phe-COO-Phe-COO-Phe-(CH₂)n—(CH2)ₒ—CF₃
alkoxy-Phe-COO-PheF-COO-Phe-(CH₂)n—(CH2)ₒ—CF₃

XV alkyl-Cyc-Cyc-CH₂CH₂-Phe-(CH₂)n—(CH2)ₒ—CF₃
alkyl-Cyc-Cyc-CH₂CH₂-PheF-(CH₂)n—(CH2)ₒ—CF₃
alkyl-Cyc-Cyc-CH₂CH₂-PheF₂-(CH₂)n—(CH2)ₒ—CF₃
alkoxy-Cyc-Cyc-CH₂CH₂-Phe-(CH₂)n—(CH2)ₒ—CF₃
alkoxy-Cyc-Cyc-CH₂CH₂-PheF-(CH₂)n—(CH2)ₒ—CF₃
alkanoyloxy-Cyc-Cyc-CH₂CH₂-Phe-(CH₂)n—(CH2)ₒ—CF₃
alkanoyloxy-Cyc-Cyc-CH₂CH₂-PheF-(CH₂)n—(CH2)ₒ—CF₃

The following compounds with at least one ω-CF₃-alkyl terminal group

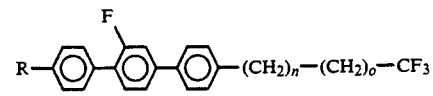

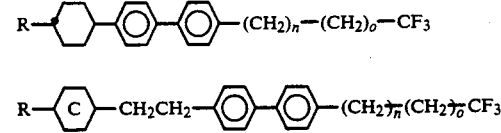

wherein
R is alkyl or alkoxy with 1-7 C atoms or (CH₂)ₙ—(CH₂)ₒ—CF₃, n+o is 1, 2, 3 or 4, especially however 2 and

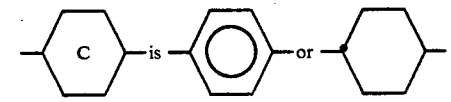

are especially preferred.
Especially preferred are further the following compounds:

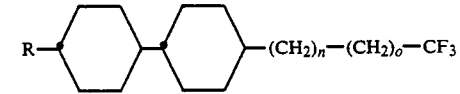

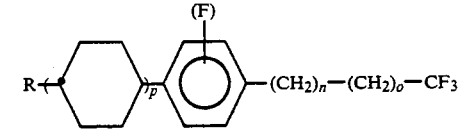

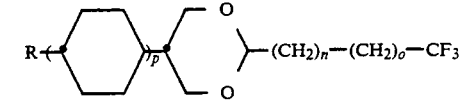

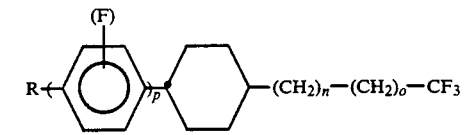

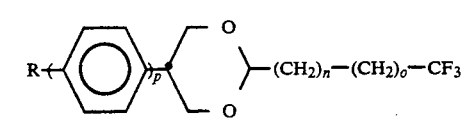

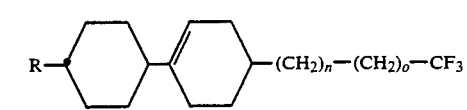

-continued

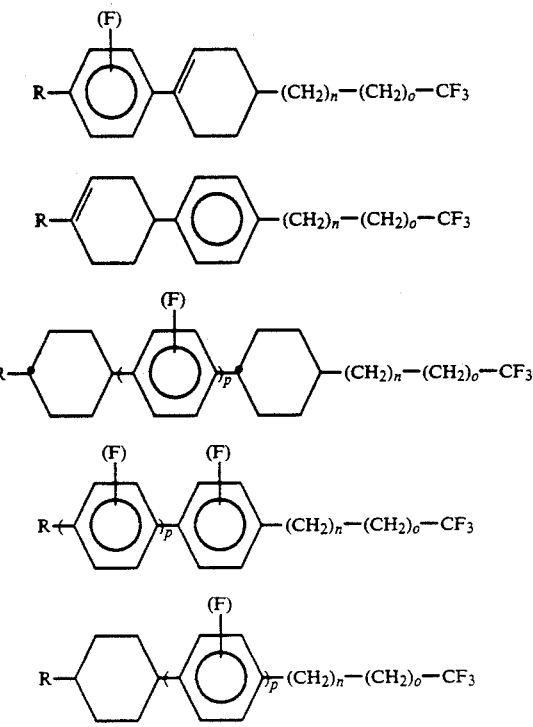

wherein
R is alkyl or alkoxy with 1-8 C atoms,
n+o is 1-6, especially however 2, 3 or 4,
p is 1 or 2, and

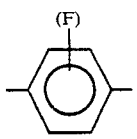

is unsubstituted or laterally monofluorinated 1,4-phenylene.

In the compounds of formula I with a ω-CF₃-alkenyl or a ω-CF₃-alkinyl terminal group the position of the ethenylene or ethinylene group can be varied along the ω-CF₃-chain. Thus it is possible to modify and optimize physical parameters like for example the elastic constants and/or the birefringence and/or the phase transition temperatures and/or other parameters with respect to the intended application.

The presence of the triple bond in the ω-CF₃-ethinylene compounds is important, as it can lead to a high birefringence of the liquid crystal phase. For such reasons compounds are preferred in which n and o are both 0, or n is 0 and m is 1 are preferred, as it is found that when the CF₃-group is directly linked to the ethine group the latter is stabilized.

Liquid crystalline compounds having a high birefringence are particularly suitable for use in a number of types of application, for example those which exploit the electrically controlled birefringence (ECB) effect (see for example M. F. Schieckel and K. Fahrenshon "App. Phys. Lett. (1971), 19, 3912"). Such compounds are also of value in other types of known liquid crystal material, such as those intended for use in thin film transistor (TFT) or superwist twisted nematic (STN) display devices. Many materials of these types, intended for such applications, and with which compounds of formula I may usefully be mixed, are known.

Compounds with a ω-CF₃-alkenyl group comprise both the (E)- and (Z)-homologues

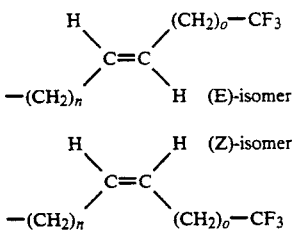

Compounds with a ω-CF₃-alkenyl group are often characterized by especially advantageous values of the elastic constants, the birefringence and/or the phase transition temperatures and these compounds are therefore preferred. Especially preferred are ω-CF₃-alkenyl terminal groups with the following values for n, o and n+o:

| n | o | n + o |
|---|---|-------|
| 1 | 0 | 1 |
| 1 | 1 | 2 |
| 1 | 2 | 3 |
| 1 | 3 | 4 |
| 1 | 5 | 6 |
| 2 | 0 | 2 |
| 2 | 1 | 3 |
| 2 | 2 | 4 |
| 2 | 4 | 6 |
| 3 | 0 | 3 |
| 3 | 1 | 4 |
| 3 | 2 | 5 |
| 4 | 0 | 4 |
| 4 | 1 | 5 |
| 4 | 2 | 6 |
| 4 | 3 | 7 |

The following smaller groups of compounds of formula I with a ω-CF₃-alkenyl resp. a ω-CF₃-alkinyl group, wherein the meaning of PheF, PheF₂, Che, Dio and Cyc is indicated above, R is an alkyl-, alkoxy-, alkanoyloxy- or alkoxycarbonyl group with 1-10 and especially 1-7 C atoms and n+o is preferably 1-7, especially however 1, 2, 3, 4 and 5, are preferred.

XVII

R-Cyc-Cyc-(CH₂)ₙ—CH=CH—(CH₂)ₒ—CF₃
R-Cyc-Che-(CH₂)ₙ—CH=CH—(CH₂)ₒ—CF₃
R-Cyc-Dio-(CH₂)ₙ—CH=CH—(CH₂)ₒ—CF₃

XVIII

R-Cyc-Phe-(CH₂)ₙ—CH=CF—(CH₂)ₒ—CF₃
R-Cyc-PheF-(CH₂)ₙ—CH=CF—(CH₂)ₒ—CF₃
R-Cyc-PheF₂-(CH₂)ₙ—CH=CF—(CH₂)ₒ—CF₃
R-Phe-Cyc-(CH₂)ₙ—CH=CF—(CH₂)ₒ—CF₃

IXX

R-Phe-Phe-(CH₂)ₙ—CH=CF—(CH₂)ₒ—CF₃
R-Phe-PheF-(CH₂)ₙ—CH=CF—(CH₂)ₒ—CF₃

XX

R-Cyc-CH₂CH₂—Cyc-(CH₂)ₙ—CH=CH—(CH₂)ₒ—CF₃

R-Cyc-CH$_2$CH$_2$—Phe-(CH$_2$)$_n$—CH=CH—(CH$_2$)$_o$—CF$_3$
R-Cyc-CH$_2$CH$_2$—PheF-(CH$_2$)$_n$—CH=CH—(CH$_2$)$_o$—CF$_3$
R-Cyc-CH$_2$CH$_2$—Dio-(CH$_2$)$_n$—CH=CH—(CH$_2$)$_o$—CF$_3$

XXI

R-Cyc-Cyc-Phe-(CH$_2$)$_n$—CH=CH—(CH$_2$)$_o$—CF$_3$
R-Cyc-Cyc-PheF-(CH$_2$)$_n$—CH=CH—(CH$_2$)$_o$—CF$_3$
R-Cyc-Cyc-PheF$_2$-(CH$_2$)$_n$—CH=CH—(CH$_2$)$_o$—CF$_3$
R-Cyc-Cyc-Che-(CH$_2$)$_n$—CH=CH—(CH$_2$)$_o$—CF$_3$
R-Cyc-Cyc-Dio-(CH$_2$)$_n$—CH=CH—(CH$_2$)$_o$—CF$_3$
R-Cyc-Phe-Cyc-(CH$_2$)$_n$—CH=CH—(CH$_2$)$_o$—CF$_3$
R-Phe-Phe-Cyc-(CH$_2$)$_n$—CH=CH—(CH$_2$)$_o$—CF$_3$
R-Phe-Cyc-Cyc-(CH$_2$)$_n$—CH=CH—(CH$_2$)$_o$—CF$_3$

XXII

R-Cyc-Phe-Phe-(CH$_2$)$_n$—CH=CH—(CH$_2$)$_o$—CF$_3$
R-Cyc-PheF-Phe-(CH$_2$)$_n$—CH=CH—(CH$_2$)$_o$—CF$_3$
R-Cyc-Phe-PheF-(CH$_2$)$_n$—CH=CH—(CH$_2$)$_o$—CF$_3$

XXIII

R-Cyc-CH$_2$CH$_2$-Phe-Phe-(CH$_2$)$_n$—CH=CH—(CH$_2$)$_o$—CF$_3$
R-Cyc-CH$_2$CH$_2$-Phe-PheF-(CH$_2$)$_n$—CH=CH—(CH$_2$)$_o$—CF$_3$
R-Cyc-CH$_2$CH$_2$-Che-Phe-(CH$_2$)$_n$—CH=CH—(CH$_2$)$_o$—CF$_3$

XXIV

R-Phe-Phe-(CH$_2$)$_n$—C≡C—(CH$_2$)$_o$—CF$_3$  XXIV
R-Phe-Phe2F-(CH$_2$)$_n$—C≡C—(CH$_2$)$_o$—CF$_3$  XXIV
R-Phe-Phe3F-(CH$_2$)$_n$—C≡C—(CH$_2$)$_o$—CF$_3$
R-Phe2F-Phe-(CH$_2$)$_n$—C≡C—(CH$_2$)$_o$—CF$_3$
R-Phe3F-Phe-(CH$_2$)$_n$—C≡C—(CH$_2$)$_o$—CF$_3$
R-Phe2F3F-Phe-(CH$_2$)$_n$—C≡C—(CH$_2$)$_o$—CF$_3$
R-Phe-Phe2F3F-(CH$_2$)$_n$—C≡C—(CH$_2$)$_o$—CF$_3$

XXV

R-Pyr-Phe-(CH$_2$)$_n$—C≡C—(CH$_2$)$_o$—CF$_3$
R-Pyr-PheF-(CH$_2$)$_n$—C≡C—(CH$_2$)$_o$—CF$_3$
R-Pyd-Phe-(CH$_2$)$_n$—C≡C—(CH$_2$)$_o$—CF$_3$
R-Pyd-PheF-(CH$_2$)$_n$—C≡C—(CH$_2$)$_o$—CF$_3$

XXVI

R-Phe(F)-OOC-Phe(F)—(CH$_2$)$_n$—C≡C—(CH$_2$)$_o$—CF$_3$
R-Phe(F)-COO-Phe(F)—(CH$_2$)$_n$—C≡C—(CH$_2$)$_o$—CF$_3$

XXVII

R-Cyc-Phe-(CH$_2$)$_n$—C≡C—(CH$_2$)$_o$—CF$_3$
R-Phe-Cyc-(CH$_2$)$_n$—C≡C—(CH$_2$)$_o$—CF$_3$
R-Che-Phe-(CH$_2$)$_n$—C≡C—(CH$_2$)$_o$—CF$_3$
R-Phe-Dio-(CH$_2$)$_n$—C≡C—(CH$_2$)$_o$—CF$_3$

XXVIII

R-Cyc-Phe-Phe-(CH$_2$)$_n$—C≡C—(CH$_2$)$_o$—CF$_3$
R-Cyc-Phe-PheF-(CH$_2$)$_n$—C≡C—(CH$_2$1 )$_o$—CF$_3$
R-Cyc-PheF-Phe-(CH$_2$)$_n$—C≡C—(CH$_2$)$_o$—CF$_3$
R-Cyc-Phe-Cyc-(CH$_2$)$_n$—C≡C—(CH$_2$)$_o$—CF$_3$
R-Phe-Cyc-Cyc-(CH$_2$)$_n$—C≡C—(CH$_2$)$_o$—CF$_3$
R-Phe-Phe-Cyc-(CH$_2$)$_n$—C≡C—(CH$_2$)$_o$—CF$_3$

XXIX

R-Phe-Phe2F-Phe-(CH$_2$)$_n$—C≡C—(CH$_2$)$_o$—CF$_3$
R-Phe-Phe3F-Phe-(CH$_2$)$_n$—C≡C—(CH$_2$)$_o$—CF$_3$
R-Phe-Phe-PheF-(CH$_2$)$_n$—C≡C—(CH$_2$)$_o$—CF$_3$
R-Phe-Phe-PheF$_2$-(CH$_2$)$_n$—C≡C—(CH$_2$)$_o$—CF$_3$
R-Phe-Phe-Phe-(CH$_2$)$_n$—C≡C—(CH$_2$)$_o$—CF$_3$

XXX

R-Cyc-Cyc-Phe-(CH$_2$)$_n$—C≡C—(CH$_2$)$_o$—CF$_3$
R-Cyc-Cyc-PheF-(CH$_2$)$_n$—C≡C—(CH$_2$)$_o$—CF$_3$
R-Cyc-Cyc-Phe-(CH$_2$)$_n$—C≡C—(CH$_2$)$_o$—CF$_3$

XXXI

R-Phe-CH$_2$CH$_2$-Phe-(CH$_2$)$_n$—C≡C—(CH$_2$)$_o$—CF$_3$
R-Phe-CH$_2$CH$_2$-PheF-(CH$_2$)$_n$—C≡C—(CH$_2$)$_o$—CF$_3$

XXXII

R-Phe-COO-Phe-(CH$_2$)$_n$—C≡C—(CH$_2$)$_o$—CF$_3$
R-Phe-COO-PheF-(CH$_2$)$_n$—C≡C—(CH$_2$)$_o$—CF$_3$
R-Phe-OOC-Phe-(CH$_2$)$_n$—C≡C—(CH$_2$)$_o$—CF$_3$
R-Phe-OOC-PheF-(CH$_2$)$_n$—C≡C—(CH$_2$)$_o$—CF$_3$
R-Phe-OOC-PheF$_2$-(CH$_2$)$_n$—C≡C—(CH$_2$)$_o$—CF$_3$

XXXIII

R-Cyc-CH$_2$CH$_2$-Phe2F-Phe-(CH$_2$)$_n$—C≡C—(CH$_2$)$_o$—CF$_3$
R-Cyc-CH$_2$CH$_2$-Phe3F-Phe-(CH$_2$)$_n$—C≡C—(CH$_2$)$_o$—CF$_3$
R-Cyc-CH$_2$CH$_2$-Phe-Phe2F-(CH$_2$)$_n$—C≡C—(CH$_2$)$_o$—CF$_3$
R-Cyc-CH$_2$CH$_2$-Phe-Phe3F-(CH$_2$)$_n$—C≡C—(CH$_2$)$_o$—CF$_3$

The following ω-CF$_3$-alkinyl compounds
R-Phe-OOC-Phe-C≡C—CF$_3$
R-Phe-COO-Phe-C≡C—CF$_3$
R-Phe-Phe-C≡C—CF$_3$
wherein
R is alkyl or alkoxy with 1–7 C atoms and the 1,4-phenylene groups may be unsubstituted or laterally mono- or difluorinated, exhibit especially advantageous properties; these compounds are furthermore preferred from the point of view of ease of preparation.

The following ω-CF$_3$-alkinyl compounds

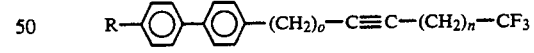

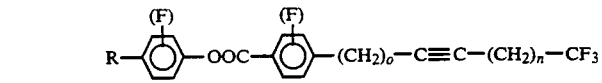

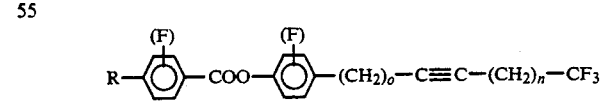

which have strong nematic tendencies are preferred.

In the ω-CF$_3$-alkinyl compounds of classes XXV–XXXII the 1,4-phenylene groups may be laterally substituted and if so mono- or difluoro substitution is preferred as this can increase the birefringence of the compound in the liquid crystal phase.

Especially preferred are further the following ω-CF₃-alkenyl compounds of formula I
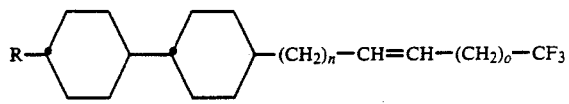
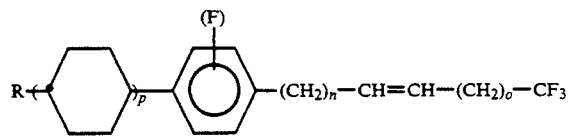
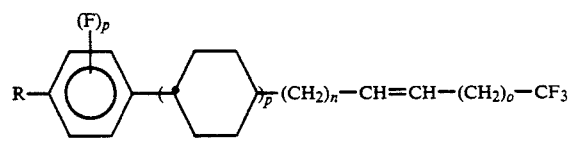
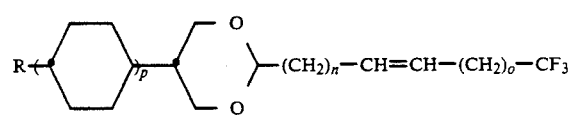
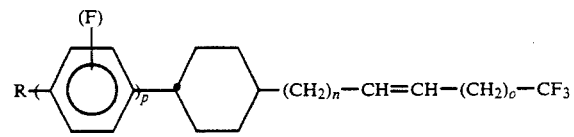
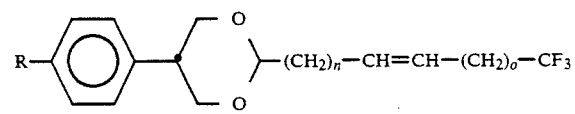
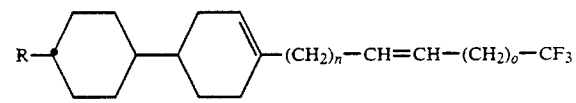
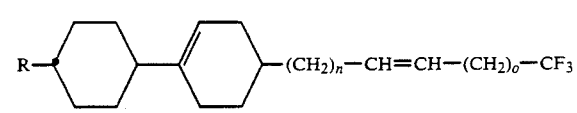
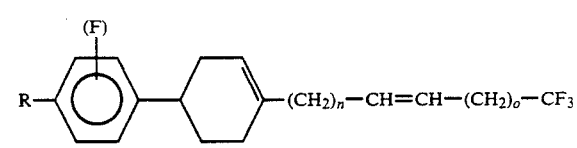
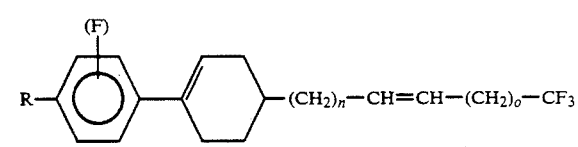
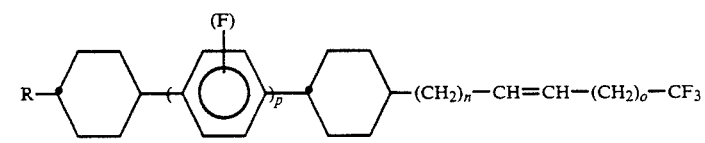
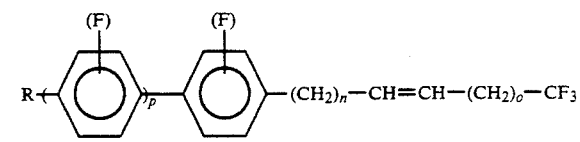

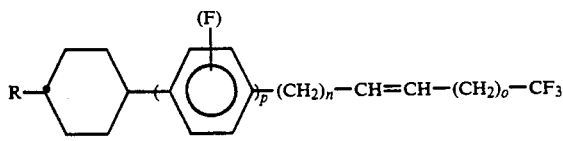

wherein
R is alkyl or alkoxy with 1–8 C atoms,
n+o is 1–6, especially, however, 2, 3 or 4,
p is 1 or 2, and

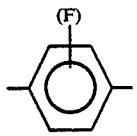

is unsubstituted or laterally monofluorinated 1,4-phenylene.

The compounds of the formula i are prepared by methods which are known per se, such as are described in the literature (for example in the standard works such as Houben-Weyl, Methoden der Organischen Chemie (Methods of Organic Chemistry), Georg-Thieme-Verlag, Stuttgart), and in particular under reaction conditions which are known and suitable for the reactions mentioned. In these reactions, it is also possible to utilize variants which are known per se and are not mentioned here in more detail.

If desired, the starting substances can also be formed in situ such that they are not isolated from the reaction mixture but are immediately reacted further to give the compounds of the formula I.

Compounds of formula I with an $\omega$-CF$_3$-alkenyl group can be obtained for example via a Wittig reaction according to the following scheme:

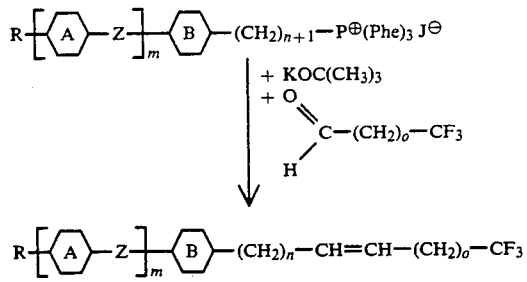

Compounds of formula I with a $\omega$-CF$_3$-alkinyl group may be prepared by a number of generally applicable routes, for example route A, B, C shown in FIG. 1 where R is as defined in formula I. The starting point for both of these routes is the known compound CF$_3$—(CH$_2$)$_o$—CCl$_2$. The zinc complex is prepared by the reaction

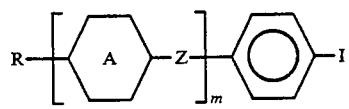

CF$_3$(CH$_2$)$_o$—C≡C.Zn described for example by W. G. Finegan and W. P. Norris, J. Org. Chem (1963), 28, 1139.

The conditions for routes A, B, C are as follows:

Route A:
A1 mix over 20 minutes DMF solvent (the zinc complex may be used without isolation as prepared above) in the presence of tetrakis (tiphenylphosphine)palladium(o) ("TTPP") at 20° C., then maintain at 50° C. for 2 hours.
A2 hydrolyse using sodium hydroxide in industrial methylated spirit (IMS) reflux, then acidify with hydrochloric acid.
A3 esterification with the phenol using dicyclohexylcarbodiimide (DCC) or trifluoroacetic anhydride in dichloromethane.
Route B: coupling reaction as step A1
Route C:
C1 esterification reaction as A3
C2 coupling reaction as A1 and B1

The individual steps of these reactions are known, albeit in some cases using homologous compounds although the overall routes are novel. Suitable stoichiometries and reaction conditions will be apparent to those skilled in the art, the hydrolysis and esterification steps A2, A3, C1 being standard. It will be appreciated that reactions A1, B1, C2 involve coupling of the ethine group to a terminal position of an iodo-substituted phenyl ring, and that therefore this reaction is of general use in the preparation of compounds of formula I with a $\omega$-CF$_3$-alkinyl group where n is 0 from phenyls of general formula II

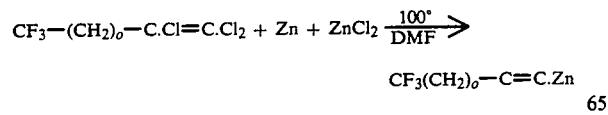

Therefore although specific ring systems are illustrated in FIG. 1, these routes may be used to prepare analogues containing other ring system. Standard separation and purification procedures may be used to isolate the products of routes A, B and C.

Compounds of formula I with a $\omega$-CF$_3$-alkinyl group wherein n≠0 can further be obtained, for example, via reacting a $\omega$-CF$_3$-alkenyl compound of formula I with bromine with subsequent elimination of HBr.

Compounds of formula I with a $\omega$-CF$_3$-alkyl group and (n+o)=o+2≧2 can be obtained by hydrogenating the $\omega$-CF$_3$-alkinyl compounds prepared via route A-C or an analogous route at a PtO$_2$ catalyst:

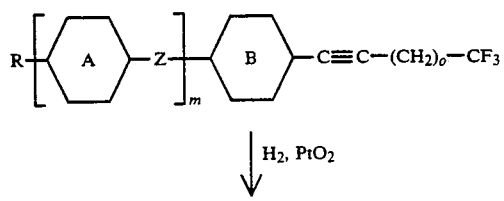

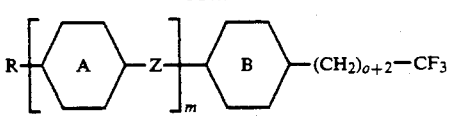

The ω-CF₃-alkyl group can further be introduced as terminal group for example by reacting

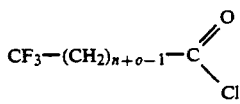

with bromobenzene via a Friedel-Crafts reaction. The carbonyl group is reduced and the bromobenzol derivative can be coupled to appropriate boronic acid derivatives thus yielding the compounds of formula I or derivatives thereof.

Compounds of formula I with a ω-CF₃-alkyl terminal group can further be prepared by hydrogenating the ω-CF₃-alkenyl compounds obtained via a Wittig reaction as mentioned above at a PtO₂ catalyst.

Compounds of formula I being obtained via boronic acid coupling of

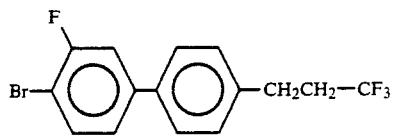

are furthermore preferred.

Compounds of formula I with a ω-CF₃-alkyl, a ω-CF₃-alkenyl or ω-CF₃-alkinyl group can further preferably be obtained by reacting

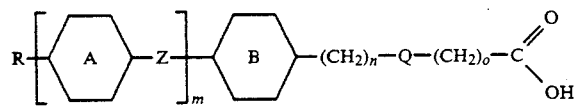

with sulfur tetrafluoride or diethylamino sulfur trifluoride (DAST).

It is further possible to convert appropriate CF₃—(CH₃)ₒ—Q—(CH₂)ₙ-terminal substituted precursors to the compounds of formula I via a metal-catalyzed cross-coupling reaction as is described, for example, in E. Poetsch, Kontakte (Darmstadt, 1988 (2), p. 15ff).

Other methods of preparing compounds of formula I are apparent to those skilled the art.

The liquid crystal media according to the invention preferably contain 2 to 40, in particular 4 to 30, components as further constituents in addition to one ore more compounds according to the invention. These media especially preferably contain 7 to 25 components in addition to one ore more compounds according to the invention. These other constituents are preferably chosen from the nematic or nematogenic (monotropic or isotropic) substances, in particular substances from the classes of azoxybenzenes, benzylideneanilines, biphenyls, terphenyls, phenyl or cyclohexyl benzoates, phenyl or cyclohexylcyclohexanecarboxylates, phenyl or cyclohexyl esters of cyclohexylbenzoid acid, phenyl or cyclohexyl esters of cyclohexylbenzoic acid, phenyl or cyclohexyl esters of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxenes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)-ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds can also be fluorinated.

The most important compounds which are possible further constituents of media according to the invention can be characterized by the formulae 1, 2, 3, 4 and 5:

$$R'—L—E—R'' \qquad 1$$

$$R'—L—COO—E—R'' \qquad 2$$

$$R'—L—OOC—E—R'' \qquad 3$$

$$R'—L—CH_2CH_2—E—R'' \qquad 4$$

$$R'—L—C≡C—E—R'' \qquad 5$$

In the formulae 1, 2, 3, 4 and 5, L and E, which can be identical or different, in each case independently of one another are a bivalent radical from the group comprising -Phe-, -Cyc-, -Phe-Phe-, -Phe-Cyc-, -Cyc-Cyc-, -Pyr-, -Dio-, -G-Phe- and -G-Cyc- and mirror images thereof, wherein Phe is 1,4-phenylene which is unsubstituted or substituted by fluorine. Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

Preferably, one of the radicals L and E is Cyc, Phe or Pyr. E is preferably Cyc, Phe or Phe-Cyc. The media according to the invention preferably contain one ore more components chosen from the compounds of the formulae 1, 2, 3, 4 and 5, wherein one of the radicals L and E is chosen from the group comprising Cyc, Phe and Pyr and the other radical is chosen from the group comprising -Phe-Phe-, -Phe-Cyc-, -Cyc-Cyc-, -G-Phe- and -G-Cyc-, and if appropriate one or more components chosen from the compounds of the formulae 1, 2, 3, 4 and 5 wherein the radicals L and E are chosen from the group comprising -Phe-Cyc-, -Cyc-Cyc-, -G-Phe- and -G-Cyc-.

R' and R'' in the compounds of the part formulae 11, 2a, 3a, 4a and 5a in each case independently of one another are alkyl, alkenyl, alkoxy, alkenyloxy or alkanoyloxy having up to 8 carbon atoms, In most of these compounds, R' and R'' differ from one another, one of these radicals usually being alkyl or alkenyl. In the compounds of the part formulae 1b, 2b, 3b, 4b and 5b, R'' is —CN, —CF₃, F, Cl, or —NCS; R here has the meaning given in the case of the compounds of the part formulae 1a to 5a, and is preferably alkyl or alkenyl. However, other variants of the envisaged substituents in the compounds of the formula 1, 2, 3, 4 and 5 can also be used.

Many such substances or mixtures thereof are commercially available. All these substances are obtainable by methods which are known from the literature or by analogous methods.

The media according to the invention preferably also contain, in addition to components from the group of compounds 1a, 2a, 3a, 4a and 5a (group 1), components from the group of compounds 1b, 2b, 3b, 4b and 5b (group 2), the properties of which are preferably as follows:

Group 1: 20 to 90%, in particular 30 to 90%,
Group 2: 10 to 80%, in particular 10 to 50%,
the sum of the proportion of the compounds according to the invention and the compounds from groups 1 and 2 being up to 100%.

Liquid crystalline media containing at least one ω-CF$_3$-alkinyl compound of formula I preferably include one ore more known compounds of general formula IIA or IIB.

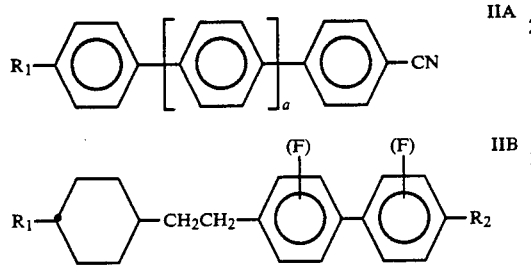

where $R_1$ is $C_1-C_{10}$ n-alkyl or alkoxy, $R_2$ is $C_1-C_{10}$ alkyl and a is 0 or 1. Preferably $R_1$ contains 3 to 8 carbon atoms. Each phenyl ring in formula IIB may carry a lateral fluorine substituent provided there is at least one fluorine in the structure. The phenyl rings in structure IIA may also carry one or more substituents, e.g. a fluorine.

Other known compounds which may be usefully be used in such a remote mixture with at least one ω-CF$_3$-alkinyl compound of formula I include those described in GB 11551043, GB 1556994, GB 1592147, GB 1587819, GB 1603076, GB 2011940, GB 2023136, GB 2027708, GB 2027027, GB 2058789, GB 2063250, GB 2071649, GB 2070594, GB 2071131, GB 2081707, GB 2079275, GB 2080820, GB 2089345, GB-A-8203798, EP 0060646, GB 2111974, U.S. Pat. No. 4,482,472, GB 2118934, U.S. Pat. No. 4,506,957, GB 2121406, EP-A-83303348.3, GB 2134110, EP-A-8430494.3, EP-A-84303240.0.

The media according to the invention preferably contain 1 to 50%, particularly preferably 5 to 30%, of compounds according to the invention. Media containing more than 40%, in particular 45 to 90%, of compounds according to the invention are furthermore preferred. The media preferably contain three, four or five compounds according to the invention.

The media according to the invention are prepared in a manner which is customary per se. As a rule, the components are dissolved in one another, preferably at elevated temperature. The liquid crystal phases according to the invention can be modified by suitable additives so that they can be used in all the types of liquid crystal display elements disclosed to date. Such additives are known to the expert and are described in detail in the literature (H. Kelker/R. Hatz, Handbook of Liquid Crystals, Verlag Chemie, Weinheim, 1980). For example, it is possible to add pleochroic dyestuffs to prepare coloured guest-host systems or substances to change the dielectric anisotropy, the viscosity and/or the orientation of the nematic phases.

The liquid crystalline media according to the invention may be nematic or smectic; preferably, however, they are nematic with the term nematic media embracing also chiral nematic=cholesteric media.

The following examples are intended to illustrate the invention without limiting it. mp.=melting point, cp.=clearing point. Percentage data above and below are percentages by weight; all the temperatures are stated in degrees Celsius. "Customary working up" means: water is added, the mixture is extracted with methylene chloride, the organic phase is separated off, dried and evaporated and the product is purified by crystallization and/or chromatography.

Further abbreviations have the following meanings: C: crystalline-solid state, S: smectic phase (the index identifies the phase type), N: nematic state, Ch: cholesteric state, I: isotropic phase. The number between two symbols indicates the transition temperature in degrees Celsuis.

EXAMPLES OF SUBSTANCES

A) ω-CF$_3$-alkyl compounds

Example 1

A mixture of 1.4 g 4-(3,3,3-trifluopropyn-1-yl)-phenyl 4-pentylbenzoate obtained by reacting 1,1,2-trichloro-3,3,3-trifluoroprop-1-ene with 4-iodi-phenyl 4-pentylbenzoate, 10 ml ethyl acetate and 0.5 g 5% Pd/C is hydrogenated at 20° and atmospheric pressure unit the reaction does not longer take up hydrogen. Customary work-up gives
4-(3,3,3-trifluoropropylphenyl) 4-pentylbenzoate exhibiting the following physical data: C 54 N (5.5) I The following compounds are prepared analogously:
4-(3,3,3-trifluoropropylphenyl) 4-ethylbenzoate
4-(3,3,3-trifluoropropylphenyl) 4-propylbenzoate
4-(3,3,3-trifluoropropylphenyl) 4-butylbenzoate
4-(3,3,3-trifluoropropylphenyl) 4-hexylbenzoate
4-(3,3,3-trifluoropropylphenyl) 4-heptylbenzoate
4-(3,3,3-trifluoropropylphenyl) 4-octylbenzoate
4-(3,3,3-trifluoropropylphenyl) 4-ethoxybenzoate
4-(3,3,3-trifluoropropylphenyl) 4-propoxybenzoate
4-(3,3,3-trifluoropropylphenyl) 4-butoxybenzoate
4-(3,3,3-trifluoropropylphenyl) 4-pentoxybenzoate
4-(3,3,3-trifluoropropylphenyl) 4-hexoxybenzoate
4-(3,3,3-trifluoropropylphenyl) 4-heptoxybenzoate
4-(3,3,3-trifluorobutylphenyl) 4-(3,3,3-trifluoropropyl)-benzoate 4-(4,4,4-trifluorobutylphenyl) 4-ethylbenzoate
4-(4,4,4-trifluorobutylphenyl) 4-propylbenzoate
4-(4,4,4-trifluorobutylphenyl) 4-butylbenzoate
4-(4,4,4-trifluorobutylphenyl) 4-pentylbenzoate
4-(4,4,4-trifluorobutylphenyl) 4-hexylbenzoate
4-(4,4,4-trifluorobutylphenyl) 4-heptylbenzoate
4-(4,4,4-trifluorobutylphenyl) 4-octylbenzoate
4-(4,4,4-trifluorobutylphenyl) 4-nonylbenzoate
4-(4,4,4-trifluorobutylphenyl) 4-ethoxybenzoate
4-(4,4,4-trifluorobutylphenyl) 4-propoxybenzoate
4-(4,4,4-trifluorobutylphenyl) 4-butoxybenzoate
4-(4,4,4-trifluorobutylphenyl) 4-pentoxybenzoate
4-(4,4,4-trifluorobutylphenyl) 4-hexoxybenzoate
4-(4,4,4-trifluorobutylphenyl) 4-heptoxybenzoate
4-(4,4,4-trifluorobutylphenyl) 4-(4,4,4-trifluorobutyl)-benzoate 4-(5,5,5-trifluoropentylphenyl) 4-ethylbenzoate
4-(5,5,5-trifluoropentylphenyl) 4-propylbenzoate
4-(5,5,5-trifluoropentylphenyl) 4-butylbenzoate
4-(5,5,5-trifluoropentylphenyl) 4-pentylbenzoate
4-(5,5,5-trifluoropentylphenyl) 4-hexylbenzoate
4-(5,5,5-trifluoropentylphenyl) 4-heptylbenzoate
4-(5,5,5-trifluoropentylphenyl) 4-octylbenzoate
4-(5,5,5-trifluoropentylphenyl) 4-nonylbenzoate
4-(5,5,5-trifluoropentylphenyl) 4-ethoxybenzoate
4-(5,5,5-trifluoropentylphenyl) 4-propoxybenzoate
4-(5,5,5-trifluoropentylphenyl) 4-butoxybenzoate
4-(5,5,5-trifluoropentylphenyl) 4-pentoxybenzoate
4-(5,5,5-trifluoropentylphenyl) 4-hexoxybenzoate
4-(5,5,5-trifluoropentylphenyl) 4-heptoxybenzoate
4-(5,5,5-trifluoropentylphenyl) 4-(4,4,4-trifluorobutyl)-benzoate Example 2

0.2 mol of trans-4-(trans-4-pentylcyclohexyl)-cyclohexane methylene carboxylic acid are reacted with 0.7 mol of sulfur tetrafluoride in an autoclave at 130° C. for 15 h. to give trans-,trans-4-pentyl-4'-(2,2,2-trifluoroethyl)cyclohexylcyclohexane. The crude material is purified by crystallization and/or chromatography: cp. 65°

The following compounds are prepared analogously:
trans-,trans-4-methyl-4'-(2,2,2-trifluoroethyl)-cyclohexylcyclohexane
trans-,trans-4-ethyl-4'-(2,2,2-trifluoroethyl)-cyclohexylcyclohexane
trans-,trans-4-propyl-4'-(2,2,2-trifluoroethyl)-cyclohexylcyclohexane
trans-,trans-4-butyl-4'-(2,2,2-trifluoroethyl)-cyclohexylcyclohexane
trans-,trans-4-hexyl-4'-(2,2,2-trifluoroethyl)-cyclohexylcyclohexane
trans-,trans-4-heptyl-4'-(2,2,2-trifluoroethyl)-cyclohexylcyclohexane
trans-,trans-4-octyl-4'-(2,2,2-trifluoroethyl)-cyclohexylcyclohexane
trans-,trans-4-methoxy-4'-(2,2,2-trifluoroethyl)-cyclohexylcyclohexane
trans-,trans-4-ethoxy-4'-(2,2,2-trifluoroethyl)-cyclohexylcyclohexane
trans-,trans-4-propoxy-4'-(2,2,2-trifluoroethyl)-cyclohexylcyclohexane
trans-,trans-4-butoxy-4'-(2,2,2-trifluoroethyl)-cyclohexylcyclohexane
trans-,trans-4-pentoxy-4'-(2,2,2-trifluoroethyl)-cyclohexylcyclohexane
trans-,trans-4-hexoxy-4'-(2,2,2-trifluoroethyl)-cyclohexylcyclohexane
trans-,trans-4-heptoxy-4'-(2,2,2-trifluoroethyl)-cyclohexylcyclohexane
trans-,trans-4-octoxy-4'-(2,2,2-trifluoroethyl)-cyclohexylcyclohexane Example 3

0.05 mol of [trans-4-(trans-4-pentylcyclohexyl)-cyclohexyl]methyl-triphenyl phosphonium iodide are dissolved in 100 ml tetrahydrofuran (THF) and 0.05 mol of 4,4,4-trifluorobutyraldehyde are added. To this mixture a solution of potassium tert.-butylate in THF is added dropwise at a temperature of 0°–5° C. and the resulting mixture is stirred for one hour at room temperature. Then water and diethylether are added and the w-CF₃-alkenyl intermediate trans-,trans-4-pentyl-4'-(5,5,5-trifluoropent-1-enyl)-cyclohexylcyclohexane is extracted and purified by chromatography. The purified intermediate is dissolved in THF, 5 g of a PtO₂ catalyst are added and the intermediate is hydrogenated at atmospheric pressure. Filtering off the catalyst and distilling off the solvent gives the crude product trans-,trans-4-pentyl-4'-(5,5,5-trifluoropentyl)-cyclohexylcyclohexane which is purified by crystallization.

The following compounds are prepared analogously:
trans-,trans-4-methyl-4'-(5,5,5-trifluoropentyl)-cyclohexylcyclohexane
trans-,trans-4-ethyl-4'-(5,5,5-trifluoropentyl)-cyclohexylcyclohexane
trans-,trans-4-propyl-4'-(5,5,5-trifluoropentyl)-cyclohexylcyclohexane
trans-,trans-4-butyl-4'-(5,5,5-trifluoropentyl)-cyclohexylcyclohexane
trans-,trans-4-hexyl-4'-(5,5,5-trifluoropentyl)-cyclohexylcyclohexane
trans-,trans-4-heptyl-4'-(5,5,5-trifluoropentyl)-cyclohexylcyclohexane
trans-,trans-4-octyl-4'-(5,5,5-trifluoropentyl)-cyclohexylcyclohexane
trans-,trans-4-nonyl-4'-(5,5,5-trifluoropentyl)-cyclohexylcyclohexane
trans-,trans-4-decyl-4'-(5,5,5-trifluoropentyl)-cyclohexylcyclohexane
trans-,trans-4-methoxy-4'-(5,5,5-trifluoropentyl)-cyclohexylcyclohexane
trans-,trans-4-ethoxy-4'-(5,5,5-trifluoropentyl)-cyclohexylcyclohexane
trans-,trans-4-propoxy-4'-(5,5,5-trifluoropentyl)-cyclohexylcyclohexane
trans-,trans-4-butoxy-4'-(5,5,5-trifluoropentyl)-cyclohexylcyclohexane
trans-,trans-4-pentoxy-4'-(5,5,5-trifluoropentyl)-cyclohexylcyclohexane
trans-,trans-4-hexoxy-4'-(5,5,5-trifluoropentyl)-cyclohexylcyclohexane
trans-,trans-4-heptoxy-4'-(5,5,5-trifluoropentyl)-cyclohexylcyclohexane
trans-,trans-4-octoxy-4'-(5,5,5-trifluoropentyl)-cyclohexylcyclohexane
trans-,trans-4-nonoxy-4'-(5,5,5-trifluoropentyl)-cyclohexylcyclohexane
trans-,trans-4-decoxy-4'-(5,5,5-trifluoropentyl)-cyclohexylcyclohexane
trans-,trans-4-(2-oxapentyl)-4'-(5,5,5-trifluoropentyl)-cyclohexylcyclohexane
trans-,trans-4-(3-oxapentyl)-4'-(5,5,5-trifluoropentyl)-cyclohexylcyclohexane
trans-,trans-4-(4-oxapentyl)-4'-(5,5,5-trifluoropentyl)-cyclohexylcyclohexane
trans-,trans-4-pentanoyloxy-4'-(5,5,5-trifluoropentyl)-cyclohexylcyclohexane Example 4

According to example 3 (4-(trans-4-propylcyclohexyl)phenyl)-methyltriphenyl phosphonium iodide is reacted with 2,2,2-trifluoroacetaldehyde. The ω-CF₃-alkenyl intermediate thus obtained is hydrogenated to give 4-(trans-4-propylcyclohexyl)-1-(3,3,3-trifluoropropyl)-benzene.

The following compounds are prepared analogously:
4-(trans-4-methylcyclohexyl)-1-(3,3,3-trifluoropropyl)-benzene
4-(trans-4-ethylcyclohexyl)-1-(3,3,3-trifluoropropyl)-benzene 4-(trans-4-butylcyclohexyl)-1-(3,3,3-trifluoropropyl)-benzene
4-(trans-4-pentylcyclohexyl)-1-(3,3,3-trifluoropropyl)-benzene
4-(trans-4-hexylcyclohexyl)-1-(3,3,3-trifluoropropyl)-benzene
4-(trans-4-heptylcyclohexyl)-1-(3,3,3-trifluoropropyl)-benzene
4-(trans-4-octylcyclohexyl)-1-(3,3,3-trifluoropropyl)-benzene
4-(trans-4-nonylcyclohexyl)-1-(3,3,3-trifluoropropyl)-benzene
4-(trans-4-decylcyclohexyl)-1-(3,3,3-trifluoropropyl)-benzene
4-(trans-4-methoxycyclohexyl)-1-(3,3,3-trifluoropropyl)benzene
4-(trans-4-ethoxycyclohexyl)-1-(3,3,3-trifluoropropyl)-benzene
4-(trans-4-propoxycyclohexyl)-1-(3,3,3-trifluoropropyl)benzene
4-(trans-4-butoxycyclohexyl)-1-(3,3,3-trifluoropropyl)-benzene
4-(trans-4-pentoxycyclohexyl)-1-(3,3,3-trifluoropropyl)benzene
4-(trans-4-hexoxycyclohexyl)-1-(3,3,3-trifluoropropyl)-benzene
4-(trans-4-heptoxycyclohexyl)-1-(3,3,3-trifluoropropyl)benzene
4-(trans-4-octoxycyclohexyl)-1-(3,3,3-trifluoropropyl)-benzene
4-(trans-4-nonoxycyclohexyl)-1-(3,3,3-trifluoropropyl)-benzene
4-(trans-4-decoxycyclohexyl)-1-(3,3,3-trifluoropropyl)-benzene

Example 5

According to example 3 (trans-4-(4-propylphenyl)-cyclohexyl)-methyl-triphenyl phosphonium iodide is reacted with 2,2,2-trifluoro-acetaldehyde. The $\omega$-$CF_3$-alkenyl intermediate thus obtained is hydrogenated to give trans-4-(4-propylphenyl)-1-(3,3,3-trifluoropropyl)-cyclohexane.

The following compounds are prepared analogously:
trans-4-(4-methylphenyl)-1-(3,3,3-trifluoropropyl)-cyclohexane
trans-4-(4-ethylphenyl)-1-(3,3,3-trifluoropropyl)-cyclohexane
trans-4-(4-butylphenyl)-1-(3,3,3-trifluoropropyl)-cyclohexane
trans-4-(4-pentylphenyl)-1-(3,3,3-trifluoropropyl)-cyclohexane
trans-4-(4-hexylphenyl)-1-(3,3,3-trifluoropropyl)-cyclohexane
trans-4-(4-heptylphenyl)-1-(3,3,3-trifluoropropyl)-cyclohexane
trans-4-(4-octylphenyl)-1-(3,3,3-trifluoropropyl)-cyclohexane
trans-4-(4-nonylphenyl)-1-(3,3,3-trifluoropropyl)-cyclohexane
trans-4-(4-decylphenyl)-1-(3,3,3-trifluoropropyl)-cyclohexane
trans-4-(4-methoxyphenyl)-1-(3,3,3-trifluoropropyl)-cyclohexane
trans-4-(4-propoxyphenyl)-1-(3,3,3-trifluoropropyl)-cyclohexane
trans-4-(4-butoxyphenyl)-1-(3,3,3-trifluoropropyl)-cyclohexane
trans-4-(4-pentoxyphenyl)-1-(3,3,3-trifluoropropyl)-cyclohexane
trans-4-(4-hexoxyphenyl)-1-(3,3,3-trifluoropropyl)-cyclohexane
trans-4-(4-heptoxyphenyl)-1-(3,3,3-trifluoropropyl)-cyclohexane
trans-4-(4-octoxyphenyl)-1-(3,3,3-trifluoropropyl)-cyclohexane
trans-4-(4-nonoxyphenyl)-1-(3,3,3-trifluoropropyl)-cyclohexane
trans-4-(4-decoxyphenyl)-1-(3,3,3-trifluoropropyl)-cyclohexane

Example 6

According to example 2 4-(trans-4-(trans-4-propylcyclohexyl)-cyclohexyl)-1-(2,2,2-trifluoroethyl)-benzene is obtained from 4-(trans-4-(trans-4-propylcyclohexyl)-cyclohexyl)-phenylmethyl carboxylic acid and sulfur tetrafluoride.

The following compounds are prepared analogously:
4-(trans-4-(trans-4-methylcyclohexyl)-cyclohexyl)-1-(2,2,2-trifluoroethyl)-benzene
4-(trans-4-(trans-4-ethylcyclohexyl)-cyclohexyl)-1-(2,2,2-trifluoroethyl)-benzene
4-(trans-4-(trans-4-butylcyclohexyl)-cyclohexyl)-1-(2,2,2-trifluoroethyl)-benzene
4-(trans-4-(trans-4-pentylcyclohexyl)-cyclohexyl)-1-(2,2,2-trifluoroethyl)-benzene
4-(trans-4-(trans-4-hexylcyclohexyl)-cyclohexyl)-1-(2,2,2-trifluoroethyl)-benzene
4-(trans-4-(trans-4-heptylcyclohexyl)-cyclohexyl)-1-(2,2,2-trifluoroethyl)-benzene
4-(trans-4-(trans-4-octylcyclohexyl)-cyclohexyl)-1-(2,2,2-trifluoroethyl)-benzene
4-(trans-4-(trans-4-nonylcyclohexyl)-cyclohexyl)-1-(2,2,2-trifluoroethyl)-benzene
4-(trans-4-(trans-4-decylcyclohexyl)-cyclohexyl)-1-(2,2,2-trifluoroethyl)-benzene
4-(trans-4-(trans-4-methoxycyclohexyl)-cyclohexyl)-1-(2,2,2-trifluoroethyl)-benzene
4-(trans-4-(trans-4-ethoxycyclohexyl)-cyclohexyl)-1-(2,2,2-trifluoroethyl)-benzene
4-(trans-4-(trans-4-propoxycyclohexyl)-cyclohexyl)-1-(2,2,2-trifluoroethyl)-benzene
4-(trans-4-(trans-4-butoxycyclohexyl)-cyclohexyl)-1-(2,2,2-trifluoroethyl)-benzene
4-(trans-4-(trans-4-pentoxycyclohexyl)-cyclohexyl)-1-(2,2,2-trifluoroethyl)-benzene
4-(trans-4-(trans-4-hexoxycyclohexyl)-cyclohexyl)-1-(2,2,2-trifluoroethyl)-benzene
4-(trans-4-(trans-4-heptoxycyclohexyl)-cyclohexyl)-1-(2,2,2-trifluoroethyl)-benzene
4-(trans-4-(trans-4-octoxycyclohexyl)-cyclohexyl)-1-(2,2,2-trifluoroethyl)-benzene
4-(trans-4-(trans-4-nonoxycyclohexyl)-cyclohexyl)-1-(2,2,2-trifluoroethyl)-benzene
4-(trans-4-(trans-4-decoxycyclohexyl)-cyclohexyl)-1-(2,2,2-trifluoroethyl)-benzene

Example 7

According to example 3 [trans-4-(4-trans-4-propylcyclohexyl)-phenyl)-cyclohexyl]-methyl phosphonium iodide is reacted with 2,2,2-trifluoroacetaldehyde. The $\omega$-$CF_3$-alkenyl intermediate thus obtained is hydrogenated to give trans-4-(4-(trans-4-propylcyclohexyl)-phenyl)-1-(3,3,3-trifluoropropyl)-cyclohexane.

The following compounds are prepared analogously:

trans-4-(4-(trans-4-methylcyclohexyl)-phenyl-1-(3,3,3-trifluoropropyl)-cyclohexane
trans-4-(4-(trans-4-ethylcyclohexyl)-phenyl-1-(3,3,3-trifluoropropyl)-cyclohexane
trans-4-(4-(trans-4-butylcyclohexyl)-phenyl-1-(3,3,3-trifluoropropyl)-cyclohexane
trans-4-(4-(trans-4-pentylcyclohexyl)-phenyl-1-(3,3,3-trifluoropropyl)-cyclohexane
trans-4-(4-(trans-4-hexylcyclohexyl)-phenyl-1-(3,3,3-trifluoropropyl)-cyclohexane
trans-4-(4-(trans-4-heptylcyclohexyl)-phenyl-1-(3,3,3-trifluoropropyl)-cyclohexane
trans-4-(4-(trans-4-octylcyclohexyl)-phenyl-1-(3,3,3-trifluoropropyl)-cyclohexane
trans-4-(4-(trans-4-nonylcyclohexyl)-phenyl-1-(3,3,3-trifluoropropyl)-cyclohexane
trans-4-(4-(trans-4-decylcyclohexyl)-phenyl-1-(3,3,3-trifluoropropyl)-cyclohexane
trans-4-(4-(trans-4-methoxycyclohexyl)-phenyl-1-(3,3,3-trifluoropropyl)-cyclohexane
trans-4-(4-(trans-4-ethoxycyclohexyl)-phenyl-1-(3,3,3-trifluoropropyl)-cyclohexane
trans-4-(4-(trans-4-propoxycyclohexyl)-phenyl-1-(3,3,3-trifluoropropyl)-cyclohexane
trans-4-(4-(trans-4-butoxycyclohexyl)-phenyl-1-(3,3,3-trifluoropropyl)-cyclohexane
trans-4-(4-(trans-4-pentoxycyclohexyl)-phenyl-1-(3,3,3-trifluoropropyl)-cyclohexane
trans-4-(4-(trans-4-hexoxycyclohexyl)-phenyl-1-(3,3,3-trifluoropropyl)-cyclohexane
trans-4-(4-(trans-4-heptoxycyclohexyl)-phenyl-1-(3,3,3-trifluoropropyl)-cyclohexane
trans-4-(4-(trans-4-octoxycyclohexyl)-phenyl-1-(3,3,3-trifluoropropyl)-cyclohexane
trans-4-(4-(trans-4-nonoxycyclohexyl)-phenyl-1-(3,3,3-trifluoropropyl)-cyclohexane
trans-4-(4-(trans-4-decoxycyclohexyl)-phenyl-1-(3,3,3-trifluoropropyl)-cyclohexane Example 8

0.1 mol of 3,3,3-trifluoropropyl-triphenyl-phosphoniumbromide, which can be obtained by reacting 1,1,1-trifluoro-2-bromo-propane and phosphor-triphenyl (see Hanack, Synthesis (1989) 685), are dissolved in 300 ml diethylether and a solution of 0.1 mol of n-butyllithium in n-hexane is added dropwise. This mixture is stirred for half an hour and then a solution of 0.1 mol of trans-,trans-4-propyl-4'-methanoyl-cyclohexylcyclohexane in diethylether is added. The resulting mixture is stirred for 15 h. at room temperature. Working-up and hydrogenation as described in example 3 gives trans-,trans-4-propyl-4'-(4,4,4-trifluorobutyl)-cyclohexylcyclohexane.

The following compounds are prepared analogously:
trans-,trans-4-methyl-4'-(4,4,4-trifluorobutyl)-cyclohexylcyclohexane
trans-,trans-4-ethyl-4'-(4,4,4-trifluorobutyl)-cyclohexylcyclohexane
trans-,trans-4-butyl-4'-(4,4,4-trifluorobutyl)-cyclohexylcyclohexane
trans-,trans-4-pentyl-4'-(4,4,4-trifluorobutyl)-cyclohexylcyclohexane
trans-,trans-4-hexyl-4'-(4,4,4-trifluorobutyl)-cyclohexylcyclohexane
trans-,trans-4-heptyl-4'-(4,4,4-trifluorobutyl)-cyclohexylcyclohexane
trans-,trans-4-octyl-4'-(4,4,4-trifluorobutyl)-cyclohexylcyclohexane
trans-,trans-4-nonyl-4'-(4,4,4-trifluorobutyl)-cyclohexylcyclohexane
trans-,trans-4-decyl-4'-(4,4,4-trifluorobutyl)-cyclohexylcyclohexane
trans-,trans-4-methoxy-4'-(4,4,4-trifluorobutyl)-cyclohexylcyclohexane
trans-,trans-4-ethoxy-4'-(4,4,4-trifluorobutyl)-cyclohexylcyclohexane
trans-,trans-4-propoxy-4'-(4,4,4-trifluorobutyl)-cyclohexylcyclohexane
trans-,trans-4-butoxy-4'-(4,4,4-trifluorobutyl)-cyclohexylcyclohexane
trans-,trans-4-pentoxy-4'-(4,4,4-trifluorobutyl)-cyclohexylcyclohexane
trans-,trans-4-hexoxy-4'-(4,4,4-trifluorobutyl)-cyclohexylcyclohexane
trans-,trans-4-heptoxy-4'-(4,4,4-trifluorobutyl)-cyclohexylcyclohexane
trans-,trans-4-octoxy-4'-(4,4,4-trifluorobutyl)-cyclohexylcyclohexane
trans-,trans-4-nonoxy-4'-(4,4,4-trifluorobutyl)-cyclohexylcyclohexane
trans-,trans-4-decoxy-4'-(4,4,4-trifluorobutyl)-cyclohexylcyclohexane
trans-,trans-4-(2-oxahexyl)-4'-(4,4,4-trifluorobutyl)-cyclohexylcyclohexane
trans-,trans-4-(3-oxahexyl)-4'-(4,4,4-trifluorobutyl)-cyclohexylcyclohexane
trans-,trans-4-(4-oxahexyl)-4'-(4,4,4-trifluorobutyl)-cyclohexylcyclohexane
trans-,trans-4-(5-oxahexyl)-4'-(4,4,4-trifluorobutyl)-cyclohexylcyclohexane
trans-,trans-4-propanoyloxy-4'-(4,4,4-trifluorobutyl)-cyclohexylcyclohexane Example 9

A mixture of 0.02 mol of 2-(trans-4-pentylcyclohexyl)-propane-1,3-diol, 0.02 mol of 4,4,4-trifluorobutyraldehyde, 0.01 g of p-toluenesulfonic acid and 20 ml of toluene is boiled under a water separator and is then cooled, washed with water and evaporated. Purification by chromatography in a customary manner gives trans-2-(trans-4-pentylcyclohexyl)-4-(4,4,4-trifluorobutyl)-1,3-dioxane.

The following compounds are prepared analogously:
trans-2-(trans-4-methylcyclohexyl)-5-(4,4,4-trifluorobutyl)-1,3-dioxane
trans-2-(trans-4-ethylcyclohexyl)-5-(4,4,4-trifluorobutyl)-1,3-dioxane
trans-2-(trans-4-propylcyclohexyl)-5-(4,4,4-trifluorobutyl)-1,3-dioxane
trans-2-(trans-4-butylcyclohexyl)-5-(4,4,4-trifluorobutyl)-1,3-dioxane
trans-2-(trans-4-hexylcyclohexyl)-5-(4,4,4-trifluorobutyl)-1,3-dioxane
trans-2-(trans-4-heptylcyclohexyl)-5-(4,4,4-trifluorobutyl)-1,3-dioxane
trans-2-(trans-4-octylcyclohexyl)-5-(4,4,4-trifluorobutyl)-1,3-dioxane
trans-2-(trans-4-methoxycyclohexyl)-5-(4,4,4-trifluorobutyl)-1,3-dioxane
trans-2-(trans-4-ethoxycyclohexyl)-5-(4,4,4-trifluorobutyl)-1,3-dioxane
trans-2-(trans-4-propoxycyclohexyl)-5-(4,4,4-trifluorobutyl)-1,3-dioxane
trans-2-(trans-4-butoxycyclohexyl)-5-(4,4,4-trifluorobutyl)-1,3-dioxane trans-2-(trans-4-pentoxycyclohexyl)-5-(4,4,4-trifluorobutyl)-1,3-dioxane
trans-2-(trans-4-hexoxycyclohexyl)-5-(4,4,4-trifluorobutyl)-1,3-dioxane
trans-2-(trans-4-heptoxycyclohexyl)-5-(4,4,4-trifluorobutyl)-1,3-dioxane
trans-2-(trans-4-octoxycyclohexyl)-5-(4,4,4-trifluorobutyl)-1,3-dioxane
trans-2-(trans-4-(trans-4-methylcyclohexyl)-cyclohexyl)-5-(4,4,4-trifluorobutyl)-1,3-dioxane
trans-2-(trans-4-(trans-4-ethylcyclohexyl)-cyclohexyl)-5-(4,4,4-trifluorobutyl)-1,3-dioxane
trans-2-(trans-4-(trans-4-propylcyclohexyl)-cyclohexyl)-5-(4,4,4-trifluorobutyl)-1,3-dioxane
trans-2-(trans-4-(trans-4-butylcyclohexyl)-cyclohexyl)-5-(4,4,4-trifluorobutyl)-1,3-dioxane
trans-2-(trans-4-(trans-4-pentylcyclohexyl)-cyclohexyl)-5-(4,4,4-trifluorobutyl)-1,3-dioxane
trans-2-(trans-4-(trans-4-hexylcyclohexyl)-cyclohexyl)-5-(4,4,4-trifluorobutyl)-1,3-dioxane
trans-2-(trans-4-(trans-4-heptylcyclohexyl)-cyclohexyl)-5-(4,4,4-trifluorobutyl)-1,3-dioxane
trans-2-(trans-4-(trans-4-octylcyclohexyl)-cyclohexyl)-5-(4,4,4-trifluorobutyl)-1,3-dioxane
trans-2-(trans-4-(trans-4-methoxycyclohexyl)-cyclohexyl)-5-(4,4,4-trifluorobutyl)-1,3-dioxane
trans-2-(trans-4-(trans-4-ethoxycyclohexyl)-cyclohexyl)-5-(4,4,4-trifluorobutyl)-1,3-dioxane
trans-2-(trans-4-(trans-4-propoxycyclohexyl)-cyclohexyl)-5-(4,4,4-trifluorobutyl)-1,3-dioxane
trans-2-(trans-4-(trans-4-butoxycyclohexyl)-cyclohexyl)-5-(4,4,4-trifluorobutyl)-1,3-dioxane
trans-2-(trans-4-(trans-4-pentoxycyclohexyl)-cyclohexyl)-5-(4,4,4-trifluorobutyl)-1,3-dioxane
trans-2-(trans-4-(trans-4-hexoxycyclohexyl)-cyclohexyl)-5-(4,4,4-trifluorobutyl)-1,3-dioxane
trans-2-(trans-4-(trans-4-heptoxycyclohexyl)-cyclohexyl)-5-(4,4,4-trifluorobutyl)-1,3-dioxane
trans-2-(trans-4-(trans-4-octoxycyclohexyl)-cyclohexyl)-5-(4,4,4-trifluorobutyl)-1,3-dioxane Example 10 trans-2-(4-propylphenyl)-5-(3,3,3-trifluoropropyl)-1,3-dioxane is obtained by reacting 4-propylbenzaldehyde with 2-(3,3,3-trifluoropropyl)-propane-1,3-diol according to example 5.

The following compounds are prepared analogously:
trans-2-(4-methylphenyl)-5-(3,3,3-trifluoropropyl)-1,3-dioxane
trans-2-(4-ethylphenyl)-5-(3,3,3-trifluoropropyl)-1,3-dioxane
trans-2-(4-butylphenyl)-5-(3,3,3-trifluoropropyl)-1,3-dioxane
trans-2-(4-pentylphenyl)-5-(3,3,3-trifluoropropyl)-1,3-dioxane
trans-2-(4-hexylphenyl)-5-(3,3,3-trifluoropropyl)-1,3-dioxane
trans-2-(4-heptylphenyl)-5-(3,3,3-trifluoropropyl)-1,3-dioxane
trans-2-(4-octylphenyl)-5-(3,3,3-trifluoropropyl)-1,3-dioxane
trans-2-(4-methoxyphenyl)-5-(3,3,3-trifluoropropyl)-1,3-dioxane
trans-2-(4-ethoxyphenyl)-5-(3,3,3-trifluoropropyl)-1,3-dioxane
trans-2-(4-propoxyphenyl)-5-(3,3,3-trifluoropropyl)-1,3-dioxane
trans-2-(4-butoxyphenyl)-5-(3,3,3-trifluoropropyl)-1,3-dioxane
trans-2-(4-pentoxyphenyl)-5-(3,3,3-trifluoropropyl)-1,3-dioxane
trans-2-(4-hexoxyphenyl)-5-(3,3,3-trifluoropropyl)-1,3-dioxane
trans-2-(4-heptoxyphenyl)-5-(3,3,3-trifluoropropyl)-1,3-dioxane
trans-2-(4-octoxyphenyl)-5-(3,3,3-trifluoropropyl)-1,3-dioxane B) ω-CF₃-alkenyl compounds Example 11 trans-,trans-4-pentyl-4'-(5,5,5-trifluoropent-1-enyl)-cyclohexylcyclohexane is prepared analogously to example 3 with the hydrogenation step being omitted. This and the following compounds comprise both the (E)- and (Z)-isomers which can be separated by chromatography and/or crystallization.

The following compounds are prepared analogously:
trans-,trans-4-methyl-4'-(5,5,5-trifluoropent-1-enyl)-cyclohexylcyclohexane
trans-,trans-4-ethyl-4'-(5,5,5-trifluoropent-1-enyl)-cyclohexylcyclohexane
trans-,trans-4-propyl-4'-(5,5,5-trifluoropent-1-enyl)-cyclohexylcyclohexane
trans-,trans-4-butyl-4'-(5,5,5-trifluoropent-1-enyl)-cyclohexylcyclohexane
trans-,trans-4-hexyl-4'-(5,5,5-trifluoropent-1-enyl)-cyclohexylcyclohexane
trans-,trans-4-heptyl-4'-(5,5,5-trifluoropent-1-enyl)-cyclohexylcyclohexane
trans-,trans-4-octyl-4'-(5,5,5-trifluoropent-1-enyl)-cyclohexylcyclohexane
trans-,trans-4-methoxy-4'-(5,5,5-trifluoropent-1-enyl)-cyclohexylcyclohexane
trans-,trans-4-ethoxy-4'-(5,5,5-trifluoropent-1-enyl)-cyclohexylcyclohexane
trans-,trans-4-propoxy-4'-(5,5,5-trifluoropent-1-enyl)-cyclohexylcyclohexane
trans-,trans-4-butoxy-4'-(5,5,5-trifluoropent-1-enyl)-cyclohexylcyclohexane
trans-,trans-4-pentoxy-4'-(5,5,5-trifluoropent-1-enyl)-cyclohexylcyclohexane
trans-,trans-4-hexoxy-4'-(5,5,5-trifluoropent-1-enyl)-cyclohexylcyclohexane
trans-,trans-4-heptoxy-4'-(5,5,5-trifluoropent-1-enyl)-cyclohexylcyclohexane
trans-,trans-4-octoxy-4'-(5,5,5-trifluoropent-1-enyl)-cyclohexylcyclohexane
trans-,trans-4-(2-oxabutyl)-4'-(5,5,5-trifluoropent-1-enyl)-cyclohexylcyclohexane
trans-,trans-4-(3-oxabutyl)-4'-(5,5,5-trifluoropent-1-enyl)-cyclohexylcyclohexane
trans-,trans-4-propanoyloxy-4'-(5,5,5-trifluoropent-1-enyl)-cyclohexylcyclohexane
trans-,trans-4-propoxylcarbonyl-4'-(5,5,5-trifluoropent-1-enyl)-cyclohexylcyclohexane
trans-,trans-4-acetyloxymethyl-4'-(5,5,5-trifluoropent-1-enyl)-cyclohexylcyclohexane Example 12

According to example 3 trans-4-(4-trans-4-propylcyclohexyl)-phenyl)-1-(3,3,3-trifluoropropen-1-yl)-cyclohexane is obtained [trans-4-(4-(trans-4-propylcyclohexyl)-phenyl)-cyclohexyl]-methyl phosphonium iodide and 2,2,2-trifluoroacetaldehyde with the hydrogenation step being omitted. This and the following compounds comprise both the (E)- and (Z)-isomers which can be separated by chromatography and/or crystallization.

The following compounds are prepared analogously:
trans-4-(4-(trans-4-methylcyclohexyl)-phenyl)-1-(3,3,3-trifluoropropen-1-yl)-cyclohexane
trans-4-(4-(trans-4-ethylcyclohexyl)-phenyl)-1-(3,3,3-trifluoropropen-1-yl)-cyclohexane
trans-4-(4-(trans-4-butylcyclohexyl)-phenyl)-1-(3,3,3-trifluoropropen-1-yl)-cyclohexane
trans-4-(4-(trans-4-pentylcyclohexyl)-phenyl)-1-(3,3,3-trifluoropropen-1-yl)-cyclohexane
trans-4-(4-(trans-4-hexylcyclohexyl)-phenyl)-1-(3,3,3-trifluoropropen-1-yl)-cyclohexane
trans-4-(4-(trans-4-heptylcyclohexyl)-phenyl)-1-(3,3,3-trifluoropropen-1-yl)-cyclohexane
trans-4-(4-(trans-4-octylcyclohexyl)-phenyl)-1-(3,3,3-trifluoropropen-1-yl)-cyclohexane
trans-4-(4-(trans-4-nonylcyclohexyl)-phenyl)-1-(3,3,3-trifluoropropen-1-yl)-cyclohexane
trans-4-(4-(trans-4-decylcyclohexyl)-phenyl)-1-(3,3,3-trifluoropropen-1-yl)-cyclohexane
trans-4-(4-(trans-4-methoxycyclohexyl)-phenyl)-1-(3,3,3-trifluoropropen-1-yl)-cyclohexane
trans-4-(4-(trans-4-ethoxycyclohexyl)-phenyl)-1-(3,3,3-trifluoropropen-1-yl)-cyclohexane
trans-4-(4-(trans-4-propoxycyclohexyl)-phenyl)-1-(3,3,3-trifluoropropen-1-yl)-cyclohexane
trans-4-(4-(trans-4-butoxycyclohexyl)-phenyl)-1-(3,3,3-trifluoropropen-1-yl)-cyclohexane
trans-4-(4-(trans-4-pentoxycyclohexyl)-phenyl)-1-(3,3,3-trifluoropropen-1-yl)-cyclohexane
trans-4-(4-(trans-4-hexoxycyclohexyl)-phenyl)-1-(3,3,3-trifluoropropen-1-yl)-cyclohexane
trans-4-(4-(trans-4-heptoxycyclohexyl)-phenyl)-1-(3,3,3-trifluoropropen-1-yl)-cyclohexane
trans-4-(4-(trans-4-octoxycyclohexyl)-phenyl)-1-(3,3,3-trifluoropropen-1-yl)-cyclohexane
trans-4-(4-(trans-4-nonoxycyclohexyl)-phenyl)-1-(3,3,3-trifluoropropen-1-yl)-cyclohexane
trans-4-(4-(trans-4-decoxycyclohexyl)-phenyl)-1-(3,3,3-trifluoropropen-1-yl)-cyclohexane C) ω-CF₃-alkinyl compounds Example 13

Using route A shown in FIG. 1 the compound:

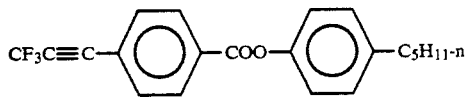

is prepared, using 4-n-pentylphenol in step A3. This compound has the properties:
K-I 62.5°, SA-I 54°, n=0.17 (extrapolated value obtained from a solution of the compound in a eutectic mixture of compounds of formula IIB)

By comparison the analogous phenylbenzoate:

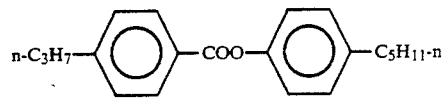

has the properties:

K-I 17° (N-I 7°), Δn=ca 0.13

Therefore, the compound of formula I has a higher Δn and an improved clearing point (liquid crystal to isotropic liquid transition) compared to that of its analogue lacking an ethine group.

Using route A a fluorinated analogue:

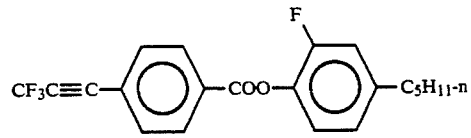

was prepared, using 2-fluoro-4-n-pentyl phenol in step A3. This compound showed liquid crystal transitions:
K-I 62.5° C. (S$_A$ - I 54° C.)

Using route B the biphenyl:

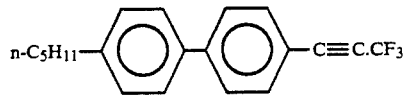

was prepared, having a melting point of 108° C. and a birefringence, measured as above, of 0.169.

Using route C, a compound

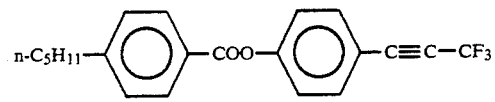

was prepared, having a liquid crystal transition K-I=77° C. and a birefringence of 0.206 measured as above.

Synthesis Details

The intermediate zinc compound CF₃C.CZn was prepared as follows: Zinc powder was cleared by stirring with 10% hydrochloric acid for 5 min, filtering, washing successively with water and IMS and then drying under vacuum. Zinc chloride was dried by fusion under vacuum. Zinc powder (90% purity, 5.8 g=0.08 mol) and zinc chloride (0.54 g=0.004 mol) were stirred in 20 ml dry DMF under a nitrogen atmosphere, and the whole mixture heated to 100° to an oil bath. 1,1,2-trichloro-3,3,3-trifluoro-propene (8.8 g, 0.044 mol) was added dropwise until the exothermic reaction began. The flask was then removed from the oil bath, and the rate of addition adjusted so as to keep the temperature between 100° and 110°. After the addition was complete, the reaction mixture was maintained at 100° for 1 hour, and then cooled to room temperature.

Route B

Step 1

The zinc reagent was prepared by the above method, using the same quantities, and cooled to room temperature. 4-pentyl-4-iodobiphenyl (11.7 g, 0.033 mol) was dissolved in 20 ml THF with tetrakis (triphenylphosphine) palladium (0) (0.5 g, 0.0043 mol), to which the solution of the zinc reagent was then added. The reaction mixture was heated to 50° for 4½ hours, cooled and poured into 100 ml 10% hydrochloric acid. The product was extracted into dichloromethane, washed with water, dried over Na$_2$SO$_4$ and distilled to dryness. The crude product was columned on 20 g silica, eluting with 40°-60° petrol, and then recrystallised from 2 volumes 60°-80° petrol.

Yield 2.45 g

Route C

Step C1

4-pentylbenzoic acid (9.6 g, 0.05 mol) and 4-iodophenol (11.0 g, 0.05 mol) were mixed in 50 ml dichloromethane with trifluoroacetic anhydride (8.5 ml, 0.06 mol) and left 18 hours at room temperature. The reaction mixture was poured into water and the organic layer separated, washed with water to neutral pH, dried over Na$_2$SO$_4$ and distilled to dryness. The crude product was columned on 20 g silica over 20 g alumina, eluting with 1:1 dichloromethane/40°-60° petrol, and then recrystallised from 50 ml IMS.

Yield 13.0 g

Step C2

4-iodophenyl 4-pentylbenzoate (12.9 g, 0.032 mol) was added dissolved in 20 ml dry THF, followed by tetrakis (triphenylphosphine) palladium (0) (0.5 g, 0.00043 mol). The reaction mixture was heated to 50° for 5 hours then cooled and poured into 100 ml hydrochloric acid. The product was extracted into dichloromethane, washed twice with water, dried over Na$_2$SO$_4$ and the solvent distilled off. The crude material was columned on 120 g silica, eluting with 4:1 40°-60° petrol/dichloromethane, and then recrystallised from 5 volumes IMS.

Yield 3.9 g HPLC 99.0%

Example 14

0.05 mol of [trans-4-(trans-4-pentylcyclohexyl)-cycylohexyl]methyl-triphenyl phosphonium iodide are dissolved in 100 ml tetrahydrofuran (THF) and 0.05 mol of 4,4,4-trifluoroacetaldhyde are added. To this mixture a solution of potassium tert.-butylate in THF is added dropwise at a temperature of 0°-5° C. and the resulting mixture is stirred for one hour at room temperature. Then water and diethylether are added and the w-CF$_3$-alkenyl intermediate trans-,trans-4-pentyl-4'-(3,3,3-trifluoroprop-1-enyl)-cyclohexylcyclohexane is extracted and purified by chromatography. The purified intermediate is dissolved in THF, 5 g of a PtO$_2$ catalyst are added and the intermediate is hydrogenated at atmospheric pressure. Filtering off the catalyst and distilling off the solvent gives the crude product trans-,trans-4-pentyl-4'-(3,3,3-trifluoropropyl)-cyclohexylcyclohexane which is purified by crystallization: mp. 50°, cp. 75°

The following compounds are prepared analogously:
trans-,trans-4-methyl-4'-(3,3,3-trifluoropropyl)-cyclohexylcyclohexane
trans-,trans-4-ethyl-4'-(3,3,3-trifluoropropyl)-cyclohexylcyclohexane
trans-,trans-4-propyl-4'-(3,3,3-trifluoropropyl)-cyclohexylcyclohexane, mp. 57°, cp. 59°
trans-,trans-4-butyl-4'-(3,3,3-trifluoropropyl)-cyclohexylcyclohexane
trans-,trans-4-hexyl-4'-(3,3,3-trifluoropropyl)-cyclohexylcyclohexane
trans-,trans-4-heptyl-4'-(3,3,3-trifluoropropyl)-cyclohexylcyclohexane
trans-,trans-4-octyl-4'-(3,3,3-trifluoropropyl)-cyclohexylcyclohexane
trans-,trans-4-nonyl-4'-(3,3,3-trifluoropropyl)-cyclohexylcyclohexane
trans-,trans-4-decyl-4'-(3,3,3-trifluoropropyl)-cyclohexylcyclohexane
trans-,trans-4-methoxy-4'-(3,3,3-trifluoropropyl)-cyclohexylcyclohexane
trans-,trans-4-ethoxy-4'-(3,3,3-trifluoropropyl)-cyclohexylcyclohexane
trans-,trans-4-propoxy-4'-(3,3,3-trifluoropropyl)-cyclohexylcyclohexane
trans-,trans-4-butoxy-4'-(3,3,3-trifluoropropyl)-cyclohexylcyclohexane
trans-,trans-4-pentoxy-4'-(3,3,3-trifluoropropyl)-cyclohexylcyclohexane
trans-,trans-4-hexoxy-4'-(3,3,3-trifluoropropyl)-cyclohexylcyclohexane
trans-,trans-4-heptoxy-4'-(3,3,3-trifluoropropyl)-cyclohexylcyclohexane
trans-,trans-4-octoxy-4'-(3,3,3-trifluoropropyl)-cyclohexylcyclohexane
trans-,trans-4-nonoxy-4'-(3,3,3-trifluoropropyl)-cyclohexylcyclohexane
trans-,trans-4-decoxy-4'-(3,3,3-trifluoropropyl)-cyclohexylcyclohexane
trans-,trans-4-(2-oxapentyl)-4'-(3,3,3-trifluoropropyl)-cyclohexylcyclohexane
trans-,trans-4-(3-oxapentyl)-4'-(3,3,3-trifluoropropyl)-cyclohexylcyclohexane
trans-,trans-4-(4-oxapentyl)-4'-(3,3,3-trifluoropropyl)-cyclohexylcyclohexane
trans-,trans-4-pentanoyloxy-4'-(3,3,3-trifluoropropyl)-cyclohexylcyclohexane

Example of Mixtures

Example A

A liquid crystalline mixture consisting of
17% of trans-1-(p-ethylphenyl)-4-propylcyclohexane
15.4% of trans-1-(p-methoxyphenol)-4-propylcyclohexane
11.6% of trans-1-(p-ethoxyphenyl)-4-propylcyclohexane
14.6% of 4-(trans-4-propylcyclohexyl)-4'-ethylbiphenyl
10.8% of 4-(trans-4-pentylcyclohexyl)-4'-ethylbiphenyl
3.8% of 4-(trans-4-propylcyclohexyl)-4'-(trans-4-propylcyclohexyl)-biphenyl
3.8% of 4-(trans-4-pentylcyclohexyl)-4'-(trans-4-propylcyclohexyl)-biphenyl
23% of 4-(3,3,3-trifluoropropylphenyl) 4-pentylbenzoate exhibits a clearing point of N 56.5 I and an optical anisotropy of $\Delta n = 0.11$.

FIG. 1

Route A

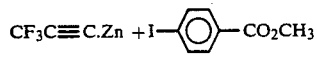

-continued
FIG. 1

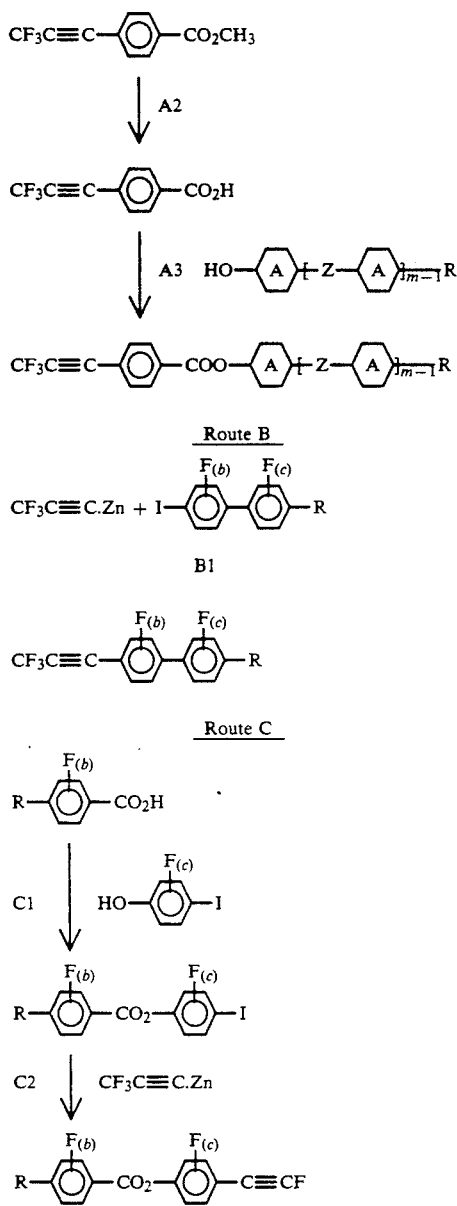

-continued
FIG. 1 b = 0, 1 or 2
c = 0, 1 or 2
(b + c) = 0, 1 or 2

We claim:

1. In a nematic liquid crystalline medium, comprising at least two liquid crystalline compounds, the improvement wherein at least one compound is a mesogenic compound with a ω-$CF_3$-alkenyl or a ω-$CF_3$-alkynyl terminal group of formula I

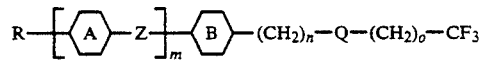

wherein
R is an unsubstituted, a mono cyano or trifluoromethyl substituted or a mono-, oligo- or polyhalogeno-substituted alkyl or alkenyl residue having 1 to 15 carbon atoms, or such a residue wherein one or more $CH_2$ groups are each independently replaced by —O—, —CO—, —CO—O—, —O—CO— or —O—CO—O with the proviso that oxygen atoms are not directly attached to each other,
the rings A and B independently are
(a) a trans-1,4-cyclohexylene group, wherein one or more two non-adjacent $CH_2$ groups may also be replaced by at least one of —O— or —S— or one or two CH groups may be replaced by N,
(b) a 1,4-phenylene group, wherein one or two CH groups may be replaced by N,
(c) 1,4-bicyclo-(2,2,2-octylene, 1,4-cyclohexenylene, napthalin-2,6-diyl or 1,3-cyclo-butylene, groups (a) and (b) being optionally substituted by one or more of halogen, cyano or methyl,
Z is independently from each other —CO—O, —O—CO—, —$CH_2CH_2$—, —$CH_2O$—, —$OCH_3$—, —C≡C, —CH=N—, —N=CH— or a single bond,
Q is —C≡C or —CH=CH—,
m is 1, 2 or 3 and
n an o are independently from each other zero or integers from 1 to 10.

2. In an electrooptical system containing a liquid crystalline medium, the improvement wherein the medium is one according to claim 1.

* * * * *